United States Patent
Cunningham, Jr. et al.

(10) Patent No.: US 6,524,811 B1
(45) Date of Patent: *Feb. 25, 2003

(54) METHODS OF INCREASING OR DECREASING CAROTENOIDS AND OTHER ISOPRENOIDS USING IPP ISOMERASE

(75) Inventors: Francis X. Cunningham, Jr., Chevy Chase, MD (US); Zairen Sun, Hyattsville, MD (US)

(73) Assignee: University of Maryland, College Park, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/937,155

(22) Filed: Sep. 25, 1997

Related U.S. Application Data

(62) Division of application No. 08/624,125, filed on Mar. 29, 1996, now Pat. No. 5,744,341.

(51) Int. Cl.[7] .............................................. C12P 23/00
(52) U.S. Cl. .......................................... 435/67; 435/233
(58) Field of Search .................... 536/23.2; 435/233, 435/320.1, 325, 67

(56) References Cited

FOREIGN PATENT DOCUMENTS

WO          98/28545    *   9/1996

OTHER PUBLICATIONS

Albrecht et al. Light–Stimulated Carotenoid Biosynthesis during Transformation of Maize Etioplasts Is Regulated by Increased Activity of Isopentenyl Pyrophosphate Isomerase. Plant Physiol. (1994) 105:529–534.*

Christensen et al. Enzymatic Synthesis of Isotopically Labeled Isoprenoid Diphosphates. Bioorganic & Medicinal Chemistry (1994) 2(7):631–637.*

LaGarde et al. Increased Production of Zeaxanthin and Other Pigments by Application of Genetic Engineering Techniques to Synechocystic sp. Strain PCC 6803. Applied and Environmetal Microbiology (2000) 66(1):64–72, Jan. 2000.*

Armstrong, Journal of Bacteriology, 1994, vol. 176, pp. 4795–4802.*

Street et al., Biochemistry, 1990, vol. 29, pp. 7531–7538.*

Campbell et al., Plant Mol. Biol. 36:323–328, 1997.*

Blanc et al., Plant Physiol. 111:652, Jun. 1996.*

Anderson et al., J. Biol. Chem. 264:19169–19175, Nov. 1989.*

Hahn et al., J. Biol. Chem. 270:11298–11303, May 1995.*

Chem. Abstr. 125:294752, 1996.*

* cited by examiner

Primary Examiner—Ponnathupura Achutamurthy
Assistant Examiner—Kathleen Kerr
(74) Attorney, Agent, or Firm—Arent Fox Kintner Plotkin & Kahn

(57) ABSTRACT

The present invention describes the DNA sequence for eukaryotic genes encoding ε cyclase, isopentenyl pyrophosphate (IPP) isomerase and β-carotene hydroxylase as well as vectors containing the same and host cells transformed with said vectors. The ε cyclase and β-carotene hydroxylase genes disclosed include those from *A. thaliana;* the IPP isomerase genes disclosed include those from *A. thaliana, H. pluvialis,* and marigold. The present invention also provides methods for controlling the ratio of various carotenoids in a host cell and for the production of novel carotenoid pigments. The present invention also provides a method for screening for eukaryotic genes encoding carotenoid biosynthesis enzymes.

10 Claims, 15 Drawing Sheets

Fig.4a

*Arabidopsis thaliana epsilon* cyclase:

```
                          acaaaaggaaataattag attcctctttctgcttgctataccttgata  48
           gaacaatataacaatggtgtaagtcttctc gctgtattcgaaattatttggaggaggaaa 108
           atggagtgtgttggggctaggaatttcgca gcaatggcggtttcaacatttccgtcatgg 168
  1         M  E  C  V  G  A  R  N  F  A    A  M  A  V  S  T  F  P  S  W
           agttgtcgaaggaaatttccagtggttaag agatacagctataggaatattcgtttcggt 228
 21         S  C  R  R  K  F  P  V  V  K    R  Y  S  Y  R  N  I  R  F  G
           ttgtgtagtgtcagagctagcggcggcgga agttccggtagtgagagttgtgtagcggtg 288
 41         L  C  S  V  R  A  S  G  G  G    S  S  G  S  K  S  C  V  A  V
           agagaagatttcgctgacgaagaagatttt gtgaaagctggtggttctgagattctattt 348
 61         R  E  D  F  A  D  E  E  D  F    V  K  A  G  G  S  K  I  L  F
           gttcaaatgcagcagaacaaagatatggat gaacagtctaagcttgttgataagttgcct 408
 81         V  Q  M  Q  Q  N  K  D  M  D    E  Q  S  K  L  V  D  K  L  P
           cctatatcaattggtgatggtgctttggat catgtggttattggttgtggtcctgctggt 468
101         P  I  S  I  G  D  G  A  L  D    H  V  V  I  G  C  G  P  A  G
           ttagccttggctgcagaatcagctaagctt ggattaaaagttggactcattggtccagat 528
121         L  A  L  A  A  E  S  A  K  L    G  L  K  V  G  L  I  G  P  D
           cttcctttactaacaattacggtgtttgg gaagatgaattcaatgatcttgggctgcaa  588
141         L  P  F  T  N  N  Y  G  V  W    E  D  E  F  N  D  L  G  L  Q
           aaatgtattgagcatgtttggagagagact attgtgtatctggatgatgacaagcctatt 648
161         K  C  I  E  H  V  W  R  E  T    I  V  Y  L  D  D  D  K  P  I
           accattggccgtgcttatggaagagttagt cgacgtttgctccatgaggagcttttgagg 708
181         T  I  G  R  A  Y  G  R  V  S    R  R  L  L  H  E  E  L  L  R
           aggtgtgtcgagtcaggtgtctcgtaccct agctcgaaagttgacagcataacagaagct 768
201         R  C  V  E  S  G  V  S  Y  L    S  S  K  V  D  S  I  T  E  A
           tctgatggccttagacttgttgcttgtgac gacaataacgtcattccctgcaggcttgcc 828
221         S  D  G  L  R  L  V  A  C  D    D  N  N  V  I  P  C  R  L  A
           actgttgcttctggagcagcttcgggaaag ctcttgcaatacgaagttggtggacctaga 888
241         T  V  A  S  G  A  A  S  G  K    L  L  Q  Y  E  V  G  G  P  R
           gtctgtgtgcaaactgcatacggcgtggag gttgaggtggaaaatagtccatatgatcca 948
261         V  C  V  Q  T  A  Y  G  V  E    V  E  V  E  N  S  P  Y  D  P
           gatcaaatggttttcatggattacagagat tatactaacgagaaagttcggagcttagaa 1008
281         D  Q  M  V  F  M  D  Y  R  D    Y  T  N  E  K  V  R  S  L  E
           gctgagtatccaacgtttctgtacgccatg cctatgacaaagtcaagactcttcttcgag 1068
301         A  E  Y  P  T  F  L  Y  A  M    P  M  T  K  S  R  L  F  F  E
           gagacatgtttggcctcaaaagatgtcatg ccctttgatttgctaaaaacgaagctcatg 1128
321         E  T  C  L  A  S  K  D  V  M    P  F  D  L  L  K  T  K  L  M
           ttaagattagatacactcggaattcgaatt ctaaagacttacgaagaggagtggtcctat 1188
341         L  R  L  D  T  L  G  I  R  I    L  K  T  Y  E  E  E  W  S  Y
           atcccagttggtggttccttgccaaacacc gaacaaaagaatctcgcctttggtgctgcc 1248
361         I  P  V  G  G  S  L  P  N  T    E  Q  K  N  L  A  F  G  A  A
           gctagcatggtacatcccgcaacaggctat tcagttgtgagatctttgtctgaagctcca 1308
381         A  S  M  V  H  P  A  T  G  Y    S  V  V  R  S  L  S  E  A  P
           aaatatgcatcagtcatcgcagagatacta agagaagagactaccaaacagatcaacagt 1368
401         K  Y  A  S  V  I  A  E  I  L    R  E  E  T  T  K  Q  I  N  S
```

Fig.4b

```
        aatatttcaagacaagcttgggatactttta tggccaccagaaaggaaaagacagagagca 1428
421     N  I  S  R  Q  A  W  D  T  L    W  P  P  E  R  K  R  Q  R  A ttctttctctttggtcttgcactcatagtt caattcgataccgaaggcattagaagcttc 1488
441     F  F  L  F  G  L  A  L  I  V    Q  F  D  T  E  G  I  R  S  F ttccgtactttcttccgccttccaaaatgg atgtggcaagggtttctaggatcaacatta 1548
461     F  R  T  F  F  R  L  P  K  W    M  W  Q  G  F  L  G  S  T  L acatcaggagatctcgttctctttgcttta tacatgttcgtcatttcaccaaacaatttg 1608
481     T  S  G  D  L  V  L  F  A  L    Y  M  F  V  I  S  P  N  N  L agaaaaggtctcatcaatcatctcatctct gatccaaccggagcaaccatgataaaaacc 1668
501     R  K  G  L  I  N  H  L  I  S    D  P  T  G  A  T  M  I  K  T tatctcaaagtatgatttacttatcaactc ttaggtttgtgtatatatatgttgatttat 1728
521     Y  L  K  V ctgaataatcgatcaaagaatggtatgtgg gttactaggaagttggaaacaaacatgtat 1788
        agaatctaaggagtgatcgaaatggagatg gaaacgaaaagaaaaaaatcagtctttgtt 1848
        ttgtggttagtg                                                 1860
```

Fig.5

```
  1  gctctttctc ctcctcctct accgatttcc gactccgcct cccgaaatcc
 51  ttatccggat tctctccgtc tcttcgattt aaacgctttt ctgtctgtta
101  cgtcgtcgaa gaacggagac agaattctcc gattgagaac gatgagagac
151  cggagagcac gagctccaca aacgctatag acgctgagta tctggcgttg
201  cgtttggcgg agaaattgga gaggaagaaa tcggagaggt ccacttatct
251  aatcgctgct atgttgtcga gctttggtat cacttctatg gctgttatgg
301  ctgtttacta cagattctct tggcaaatgg agggaggtga gatctcaatg
351  ttggaaatgt ttggtacatt tgctctctct gttggtgctg ctgttggtat
401  ggaattctgg gcaagatggg ctcatagagc tctgtggcac gcttctctat
451  ggaatatgca tgagtcacat cacaaaccaa gagaaggacc gtttgagcta
501  aacgatgttt ttgctatagt gaacgctggt ccagcgattg gtctcctctc
551  ttatggattc ttcaataaag gactcgttcc tggtctctgc tttggcgccg
601  ggttaggcat aacggtgttt ggaatcgcct acatgtttgt ccacgatggt
651  ctcgtgcaca agcgtttccc tgtaggtccc atcgccgacg tcccttacct
701  ccgaaaggtc gccgccgctc accagctaca tcacacagac aagttcaatg
751  gtgtaccata tggactgttt cttggaccca aggaattgga agaagttgga
801  ggaaatgaag agttagataa ggagattagt cggagaatca atcatacaa
851  aaaggcctcg ggctccgggt cgagttcgag ttcttgactt taaacaagtt
901  ttaaatccca aattcttttt ttgtcttctg tcattatgat catcttaaga
951  cggtct
```

Fig.6

```
                                                                                                                                      64
A.thal.          SFSS       SSTDFRLRLP KSLSGFSPSL RFKRFSVCYV VEERRQNSPI ENDERPESTS STNAIDAEYL 144
A.thal.     ALRLAEKLER KKSERSTYLI AAMLSSFGIT SMAVMAVYYR FSWQMEGGEI SMLEMFGTFA .......... LSVGAAVGME FWARWAHRAL
Alical.     .......... .......... .......... .......... .......... ..MTQFL... .......... IVVATVLVME LTAYSVHRWI
A.aurant.   .......... .......... .......... .......... .......... ..MTNFL... .......... IVVATVLVME LTAYSVHRWI
E.herb.     .......... .......... .......... .......... .......... ..ML.NSL.. .......... IVILSVIAME GIAAFTHRYI
E.ured.     .......... .......... .......... .......... .......... ..MLWIWNAL .......... IVFVTVIGME VIAALAHKYI
Consensus   ---------- ---------- ---------- ---------- ---------- ------f--- ---------- --v----ME- --A---Hr--

Predicted TM helix
                                                                                                                                     224
A.thal.     WHASL.WNMH ESHHKPREGP FELNDVFAIV NAGPAIGLLS YGFFNKGLVP GLCFGAGLGI TVDGIAYMFV HDGLVHKRFP
Alical.     MHGPLGWGWH KSHHEEHDHA LEKNDLYGVV FAVLATILFT VGAYWWPVLW WI....ALGM TVYGLIYFIL HDGLVHQRWP
A.aurant.   MHGPLGWGWH KSHHEEHDHA LEKNDLYGLV FAVIATVLFT VGWNIWAPVLW WI....ALGM TVYGLIYFVL HDGLVHQRWP
E.herb.     MHG.WGWRWH ESHHTPRKGV FELNDLFAVV FAGVAIALIA VGTAGVWPLQ WI....GCGM TVYGLLYFLV HDGLVHQRWP
E.ured.     MHG.WGWGWH LSHHEPRKGA FEVNDLYAVV FAALSILLIY LGSTGMWPLQ WI....GAGM TAYGLLYFMV HDGLVHQRWP
Consensus   -H---W--H -SHH-pr-g- fE-ND--a-V -A--ai-L-- -G-------- ------glG- -Tv-G--Y---v HDGLVH-R-P Predicted TM helix                        Predicted TM helix
                                                                                                                                     301
A.thal.     VGPIADVPYL RKVAAAHQLH HT..DKFNGV PYGLFLGPKE LEEVGGNEEL DKEISRRIKS YKKASGSGSS SSS*......
Alical.     FRYIPRRGYF RRLYQAHRLH HAVEGRDHCV SFGFIYAPP. VDKLKQDLKR SGVLRPQDER PS*....... ..........
A.aurant.   FRYIPRKGYA RRLYQAHRLH HAVEGRDHCV SFGFIYAPP. VDKLKQDLKM SGVLRAEAQE RT*....... ..........
E.herb.     FHWIPRRGYL KRLYVAHRLH HAVRGREGCV SFGFIYARK. PADLQAILRE RHGRPPKRDA AKDRPDAASP SSSSPE*...
E.ured.     FRYIPRKGYL KRLYMAHRMH HAVRGKEGCV SFGFLYAPP. LSKLQATLRE RHG..ARAGA ARDAQGGEDE PASGK*....
Consensus   ---I----Y1 r----AH-1H H--------V ---G----p- ---------- ---------- ---------- ---s------
```

Fig.7

```
  1  ccacgggtcc gcctccccgt ttttttccga tccgatctcc ggtgccgagg
 51  actcagctgt ttgttcgcgc tttctcagcc gtcaccatga ccgattctaa
101  cgatgctgga atggatgctg ttcagagacg actcatgttt gaagacgaat
151  gcattctcgt tgatgaaaat aatcgtgtgg tgggacatga cactaagtat
201  aactgtcatc tgatggaaaa gattgaagct gagaatttac ttcacagagc
251  tttcagtgtg tttttattca actccaagta tgagttgctt ctccagcaac
301  ggtcaaaaac aaaggttact ttcccacttg tgtggacaaa cacttgttgc
351  agccatcctc tttaccgtga atccgagctt attgaagaga atgtgcttgg
401  tgtaagaaat gccgcacaaa ggaagctttt cgatgagctc ggtattgtag
451  cagaagatgt accagtcgat gagttcactc ccttgggacg catgctttac
501  aaggcacctt ctgatgggaa atggggagag cacgaagttg actatctact
551  cttcatcgtg cgggatgtga agcttcaacc aaacccagat gaagtggctg
601  agatcaagta cgtgagcagg gaagagctta aggagctggt gaagaaagca
651  gatgctggcg atgaagctgt gaaactatct ccatggttca gattggtggt
701  ggataatttc ttgatgaagt ggtgggatca tgttgagaaa ggaactatca
751  ctgaagctgc agacatgaaa accattcaca agctctgaac tttccataag
801  ttttggatct tccccttccc ataataaaat taagagatga gacttttatt
851  gattacagac aaaactggca acaaaatcta ttcctaggat ttttttttgc
901  tttttattta cttttgattc atctctagtt tagttttcat cttaaaaaaa
951  aaaa
```

Fig.8

```
  1  caccaatgtc tgtttcttct ttatttaatc tcccattgat tcgcctcaga
 51  tctctcgctc tttcgtcttc ttttcttct  ttccGATTTG CCCATCGTCC
101  TCTGTCATCG ATTTCACCGA GAAAGTTACC GAATTTTCGT GCTTTCTCTG
151  GTACCGCTAT GACAGATACT AAAGATGCTG GTATGGATGC TGTTCAGAGA
201  CGTCTCATGT TTGAGGATGA ATGCATTCTT GTTGATGAAA CTGATCGTGT
251  TGTGGGGCAT GTCAGCAAGT ATAATTGTCA TCTGATGGAA AATATTGAAG
301  CCAAGAATTT GCTGCACAGG GCTTTTAGTG TATTTTTATT CAACTCGAAG
351  TATGAGTTGC TTCTCCAGCA AGGTCAAAC  ACAAAGGTTA CGTTCCCTCT
401  AGTGTGGACT AACACTTGTT GCAGCCATCC TCTTTACCGT GAATCAGAGC
451  TTATCCAGGA CAATGCACTA GGTGTGAGGA ATGCTGCACA AAGAAAGCTT
501  CTCGATGAGC TTGGTATTGT AGCTGAAGAT GTACCAGTCG ATGAGTTCAC
551  TCCCTTGGGA CGTATGCTGT ACAAGGCTCC TTCTGATGGC AAATGGGGAG
601  AGCATGAACT TGATTACTTG CTCTTCATCG TGCGAGACGT GAAGGTTCAA
651  CCAAACCCAG ATGAAGTAGC TGAGATCAAG TATGTGAGCC GGGAAGAGCT
701  GAAGGAGCTG GTGAAGAAAG CAGATGCAGG TGAGGAAGGT TTGAAACTGT
751  CACCATGGTT CAGATTGGTG GTGGACAATT TCTTGATGAA GTGGTGGGAT
801  CATGTTGAGA AAGGAACTTT GGTTGAAGCT ATAGACATGA AAACCATCCA
851  CAAACTCTGA ACATCTTTTT TTAAAGTTTT TAAATCAATC AACTTTCTCT
901  TCATCATTTT TATCTTTTCG ATGATAATAA TTTGGGATAT GTGAGACACT
951  TACAAAACTT CCAAGCACCT CAGGCAATAA TAAAGTTTGC GGCCGC
```

Fig.9

```
   1  CTCGGTAGCT GGCCACAATC GCTATTTGGA ACCTGGCCCG GCGGCAGTCC
  51  GATGCCGCGA TGCTTCGTTC GTTGCTCAGA GGCCTCACGC ATATCCCCCG
 101  CGTGAACTCC GCCCAGCAGC CAGCTGTGC  ACACGCGCGA CTCCAGTTTA
 151  AGCTCAGGAG CATGCAGATG ACGCTCATGC AGCCCAGCAT CTCAGCCAAT
 201  CTGTCGCGCG CCGAGGACCG CACAGACCAC ATGAGGGGTG CAAGCACCTG
 251  GGCAGGCGGG CAGTCGCAGG ATGAGCTGAT GCTGAAGGAC GAGTGCATCT
 301  TGGTGGATGT TGAGGACAAC ATCACAGGCC ATGCCAGCAA GCTGGAGTGT
 351  CACAAGTTCC TACCACATCA GCCTGCAGGC CTGCTGCACC GGGCCTTCTC
 401  TGTGTTCCTG TTTGACGATC AGGGGCGACT GCTGCTGCAA CAGCGTGCAC
 451  GCTCAAAAAT CACCTTCCCA AGTGTGTGGA CGAACACCTG CTGCAGCCAC
 501  CCTTTACATG GGCAGACCCC AGATGAGGTG GACCAACTAA GCCAGGTGGC
 551  CGACGGAACA GTACCTGGCG CAAAGGCTGC TGCCATCCGC AAGTTGGAGC
 601  ACGAGCTGGG GATACCAGCG CACCAGCTGC CGGCAAGCGC GTTTCGCTTC
 651  CTCACGCGTT TGCACTACTG TGCCGCGGAC GTGCAGCCAG CTGCGACACA
 701  ATCAGCGCTC TGGGGCGAGC ACGAAATGGA CTACATCTTG TTCATCCGGG
 751  CCAACGTCAC CTTGGCGCCC AACCCTGACG AGGTGGACGA AGTCAGGTAC
 801  GTGACGCAAG AGGAGCTGCG GCAGATGATG CAGCCGGACA ACGGGCTGCA
 851  ATGGTCGCCG TGGTTTCGCA TCATCGCCGC GCGCTTCCTT GAGCGTTGGT
 901  GGGCTGACCT GGACGCGGCC CTAAACACTG ACAAACACGA GGATTGGGGA
 951  ACGGTGCATC ACATCAACGA AGCGTGAAAG CAGAAGCTGC AGGATGTGAA
1001  GACACGTCAT GGGGTGGAAT TGCGTACTTG GCAGCTTCGT ATCTCCTTTT
1051  TCTGAGACTG AACCTGCAGT CAGGTCCCAC AAGGTCAGGT AAAATGGCTC
1101  GATAAAATGT ACCGTCACTT TTTGTCGCGT ATACTGAACT CCAAGAGGTC
1151  AAAAAAAAAA AAAAA
```

Fig.10

```
   1  CTCGGTAGCT GGCCACAATC GCTATTTGGA ACCTGGCCCG GCGGCAGTCC
  51  GATGCCGCGA TGCTTCGTTC GTTGCTCAGA GGCCTCACGC ATATCCCGCG
 101  CGTGAACTCC GCCCAGCAGC CCAGCTGTGC ACACGCGCGA CTCCAGTTTA
 151  AGCTCAGGAG CATGCAGCTG CTTTCCGAGG ACCGCACAGA CCACATGAGG
 201  GGTGCAAGCA CCTGGGCAGG CGGGCAGTCG CAGGATGAGC TGATGCTGAA
 251  GGACGAGTGC ATCTTGGTAG ATGTTGAGGA CAACATCACA GGCCATGCCA
 301  GCAAGCTGGA GTGTCACAAG TTCCTACCAC ATCAGCCTGC AGGCCTGCTG
 351  CACCGGGCCT TCTCTGTGTT CCTGTTTGAC GATCAGGGGC GACTGCTGCT
 401  GCAACAGCGT GCACGCTCAA AAATCACCTT CCCAAGTGTG TGGACGAACA
 451  CCTGCTGCAG CCACCCTTTA CATGGGCAGA CCCCAGATGA GGTGGACCAA
 501  CTAAGCCAGG TGGCCGACGG AACAGTACCT GGCGCAAAGG CTGCTGCCAT
 551  CCGCAAGTTG GAGCACGAGC TGGGGATACC AGCGCACCAG CTGCCGGCAA
 601  GCGCGTTTCG CTTCCTCACG CGTTTGCACT ACTGTGCCGC GGACGTGCAG
 651  CCAGCTGCGA CACAATCAGC GCTCTGGGGC GAGCACGAAA TGGACTACAT
 701  CTTGTTCATC CGGGCCAACG TCACCTTGGC GCCCAACCCT GACGAGGTGG
 751  ACGAAGTCAG GTACGTGACG CAAGAGGAGC TGCGGCAGAT GATGCAGCCG
 801  GACAACGGGC TTCAATGGTC GCCGTGGTTT CGCATCATCG CCGCGCGCTT
 851  CCTTGAGCGT TGGTGGGCTG ACCTGGACGC GGCCCTAAAC ACTGACAAAC
 901  ACGAGGATTG GGGAACGGTG CATCACATCA ACGAAGCGTG AAGGCAGAAG
 951  CTGCAGGATG TGAAGACACG TCATGGGGTG GAATTGCGTA CTTGGCAGCT
1001  TCGTATCTCC TTTTTCTGAG ACTGAACCTG CAGAGCTAGA GTCAATGGTG
1051  CATCATATTC ATCGTCTCTC TTTTGTTTTA GACTAATCTG TAGCTAGAGT
1101  CACTGATGAA TCCTTTACAA CTTTCAAAAA AAAAA
```

Fig.11

```
         1                                                              50
HPO4     MLRSLLRGLT HIPRVNSAQQ PSCAHARLQF KLRSMQMTLM QPSISANLSR
HPO5     MLRSLLRGLT HIPRVNSAQQ PSCAHARLQF KLRSMQLL.. ..........
ATDP7    MSVSSLFNLP .LIRLRSLA. LSSSFSSFRF AHRPLSSIS. PRKLPNFRAF
C brew   MS.SSMLNFT .ASRIVSLPL LSSPPSRVHL PLCFFSPISL TQRFSAKLTF
ATDP5    .......... .TGPPPRFFP IRSPVPRTQL FVRAFSAV.. ..........
S cerev. ..MTADNNSM PHGAVSSYAK LVQNQTPEDI LEEFPEIIPL QQRPN...TR 51                                                             100
         AEDRTDHMRG ASTWAGGQSQ DELMLKDECI LVDVEDNITG HASKLECHKF
         SEDRTDHMRG ASTWAGGQSQ DELMLKDECI LVDVEDNITG HASKLECHKF
         S..GTA.MTD TKDAGMDAVQ RRLMFEDECI LVDETDRVVG HVSKYNCHLM
         SSQATT.MGE VVDAGMDAVQ RRLMFEDECI LVDENDKVVG HESKYNCHLM
         .....T.MTD SNDAGMDAVQ RRLMFEDECI LVDENNRVVG HDTKYNCHLM
         SSETSNDESG ETCFSGHDEE QIKLMNENCI VLDWDDNAIG AGTKKVCHLM 101                                                            150
         LPHQPAGLLH RAFSVFLFDD QGRLLLQQRA RSKITFPSVW TNTCCSHPLH
         LPHQPAGLLH RAFSVFLFDD QGRLLLQQRA RSKITFPSVW TNTCCSHPLH
         ENIEAKNLLH RAFSVFLFNS KYELLLQQRS NTKVTFPLVW TNTCCSHPLY
         EKIESENLLH RAFSVFLFNS KYELLLQQRS ATKVTFPLVW TNTCCSHPLY
         EKIEAENLLH RAFSVFLFNS KYELLLQQRS KTKVTFPLVW TNTCCSHPLY
         ENIE.KGLLH RAFSVFIFNE QGELLLQQRA TEKITFPDLW TNTCCSHPLC 151                                                            200
         GQTPDEVDQL SQVADGTVPG AKAAAIRKLE HELGIPAHQL PA.SAFRFLT
         GQTPDEVDQL SQVADGTVPG AKAAAIRKLE HELGIPAHQL PA.SAFRFLT
         RE........ SELIQDNALG VRNAAQRKLL DELGIVAEDV PV.DEFTPLG
         RE........ SELIDENCLG VRNAAQRKLL DELGIPAEDL PV.DQFIPLS
         RE........ SELIEENVLG VRNAAQRKLF DELGIVAEDV PV.DEFTPLG
         ID...DELGL KGKLDDKIKG AITAAVRKLD HELGIPEDET KTRGKFHFLN 201                                                            250
         RLHYCAADVQ PAATQSALWG EHEMDYILFI ....RANVTL APNPDEVDEV
         RLHYCAADVQ PAATQSALWG EHEMDYILFI ....RANVTL APNPDEVDEV
         RMLY...... .KAPSDGKWG EHELDYLLFI ....VRDVKV QPNPDEVAEI
         RILY...... .KAPSDGKWG EHELDYLLFI ....IRDVNL DPNPDEVAEV
         RMLY...... .KAPSDGKWG EHEVDYLLFI ....VRDVKL QPNPDEVAEI
         RIHY...... .MAPSNEPWG EHEIDYILFY KINAKENLTV NPNVNEVRDF 251                                                            300
         RYVTQEELRQ MMQ....PDN GLQWSPWFRI IAARFLERWW ADLDAALNTD
         RYVTQEELRQ MMQ....PDN GLQWSPWFRI IAARFLERWW ADLDAALNTD
         KYVSREELKE LVKKADAGEE GLKLSPWFRL VVDNFLMKWW DHVEKGTLVE
         KYMNRDDLKE LLRKADAEEE GVKLSPWFRL VVDNFLFKWW DHVEKGSLKD
         KYVSREELKE LVKKADAGDE AVKLSPWFRL VVDNFLMKWW DHVEKGTITE
         KWVSPNDLKT MF.....ADP SYKFTPWFKI ICENYLFNWW EQLDDLSEVE 301
         KHEDWGTVHH INEA*
         KHEDWGTVHH INEA*
         A.IDMKTIHK L*
         A.ADMKTIHK L*
         A.ADMKTIHK L*
         NDRQ...IHR ML*
```

Fig.12

```
  1  ccaaaaacaa ctcaaatctc ctccgtcgct cttactccgc catgggtgac
 51  gactccggca tggatgctgt tcagcgacgt ctcatgtttg acgatgaatg
101  cattttggtg gatgagtgtg acaatgtggt gggacatgat accaaataca
151  attgtcactt gatggagaag attgaaacag gtaaaatgct gcacagagca
201  ttcagcgttt ttctattcaa ttcaaaatac gagttacttc ttcagcaacg
251  gtctgcaacc aaggtgacat ttcctttagt atggaccaac acctgttgca
301  gccatccact ctacagagaa tccgagcttg ttcccgaaac gcctgagaga
351  atgctgcaca gaggaxxxxx xxxxxxxxxx xxxxxxxxxx xxxxxxxxxx
401  xxxxxxxxxx xxxxxxxxxx xxxxxxxxxx xxxxxxxxxx xxxxxxxxxx
451  xxxxxxxxxx xxxxxxxxxx xxxxxxxxxx xxxxxxxxxx xxxxxxxxxx
501  xxxxxxxxxx xxxxxxxxxx xxxxxxxxxx xxxxxxxxxx xxxxxxxxxx
551  xxxxxxxxxx xxxxxxxxxx xxxxxxxxxx xxxxxxxxxx xxxxxxxxxx
601  xxxxxxxxxx xxxxxxxxxx xxxxxxxxxx xxxxxxxxxx xxxxxxxxxx
651  xxxxxxxxxx xxxxxxxxxx xxxxxxxxxx tcatgtgcaa aagggtacac
701  tcactgaatg caatttgata tgaaaaccat acacaagctg atatagaaac
751  acccctcaa ccgaaaagca agcctaataa ttcgggttgg gtcgggtcta
801  ccatcaattg ttttttttctt ttaacaactt ttaatctcta tttgagcatg
851  ttgattcttg tcttttgtgt gtaagatttt gggtttcgtt tcagttgtaa
901  taatgaacca ttgatggttt gcaatttcaa gttcctatcg acatgtagtg
951  atctaaaaaa
```

Fig. 13a

```
                         1                                                                                          70
Plant beta               ..........  ...MDTLLkT  PN-LeFl-p-  -HG.....F-  vk.-S-f-s-  k---fG--K-  Ce--g---vc
A.t. epsilon             MECVGARNFA  AMAVSTFPSW  SCRRKFPVVK  RYSYRNIRFG  LCSVRASGGG  SSGSESCVAV  REDFADEEDF
Consensus                ----------  ----------  ------T---  ---------F  ----F-----  ----------  -E--------
                                              Cyanobacterial enzyme begins ——————→

71                                                                                         140
Plant beta               vk---SsALLe  LVPETKKENL  DFELPmYDp.  ...S.Kg-VV  DLAvVGGGPA  GLAVAQQVSE  AGLSVcSIDP
A.t. epsilon             VKAGGSEIL.  FVQMQQNKDM  DEQSKLVDKL  PPISIGDGAL  DHVVIGCGPA  GLALAAESAK  LGLKVGLIGP
Consensus                VK---S--L-  ---V------  D------D--  -------S--  D-V-G-GPA   GLA-A-----  -GL-V--I-P
                         ←———— Possible subunit interaction domain ————→        ←— Dinucleotide-binding signature —↑

141                                                                                        210
Plant beta               .-PKLIWPNNN  YGVWDEFEA   MDLLDCLDaT  WSGa-VYidd  liCnDG-tIQ  AtVLDATGF   SR-.LVQYDK  PYnPGY.QVA  YGIlAEVeeH
A.t. epsilon             DLP...FTNN  YGVWEDEFND  LGLQKCIEHV  WRETIVYLDD  VACDDNNVIP  CRLATVASGA  ASGKLLQYEV  GGPRVCVQTA  YGVEVEVENS
Consensus                --P------   NN YGVW-DEF--  -----L--C---  W-----VY--DD  --C-D---I-  ------A-G-  -----L-QY--  -------Q-A  YG---EV---
                         ←——— Conserved region #1 ———→

211                                                                                        280
Plant beta               VKFHqaKViK  ViHE.E-kSm
A.t. epsilon             VSYLSSKVDS  ITEASDGLRL
Consensus                V-----KV--  ----------

281                                                                                        350
Plant beta               PFD--KMVfM  DWRDsHL-nn  -eLKERNs-i  PTFLYAMPFS  SNrIFLEETS  LVARPGLrmd  DIQERMvARL
A.t. epsilon             PYDPDQMVFM  DYRDY..TNE  .KVRSLEAEY  PTFLYAMPMT  KSRLFFEETC  LASKDVMPFD  LLKTKLMLRL
Consensus                P-D---MVFM  D-RD------  -N--------  PTFLYAMP--  --R-F-EET-  L-------D-  ---------RL
                         ←— Conserved region #2 —→                ←— Conserved region #3 —↑
```

Fig. 13b

```
             351
Plant beta   -HLGIkVKsI EEDEhCvIPM GGpLPVlPQR VVGiGGTAGm VHPSTGYMVA RTLAAAPvVA NAIi-YLgSe
A.t. epsilon DTLGIRILKT YEEEWSYIPV GGSLPNTEQK NLAFGAAASM VHPATGYSVV RSLSEAPKYA SVIAEILREE   420
Consensus    --LGI----- -E-E---IP- GG-LP----Q- ----G--A-M VHP-TGY-V- R-L--AP--A --I---L--E
                                                         ↑
                                                  Conserved region #4    Predicted TM helix 421
Plant beta   -s-s..G-eL SaeVWkDLWP IERRRQREFF CFGMDILLKL DLpATRRFFD AFFDLePrYW
A.t. epsilon TTKQINSN.I SRQAWDTLWP PERKRQRAFF LFGLALIVQF DTEGIRSFFR TFFRLPKWMW              480
Consensus    ---------- S---W--LWP -ER-RQR-FF -FG------ D----R-FF- -FF-L----W
                         ↑
                 Conserved region #5                                                ↑

481
Plant beta   HGFLSSRLfL PELivFGLSL FShASNTSR- EIMTK.GT-P Lv-MINNLlQ D-e
A.t. epsilon QGFLGSTLTS GDLVLFALYM FVISPNNLRK GLINHLISDP TGATMIKTYL KV.                    533
Consensus    -GFL-S-L-- --L--F-L-- F-----N--R- F-----L--- ---------- ---
             _____
             Predicted TM helix
```

METHODS OF INCREASING OR DECREASING CAROTENOIDS AND OTHER ISOPRENOIDS USING IPP ISOMERASE

This is a Division, of application Ser. No. 08/624,125 filed on Mar. 29, 1996, now U.S. Pat. No. 5,744,341.

BACKGROUND OF THE INVENTION

1. Field of the Invention

The present invention describes the DNA sequence for eukaryotic genes encoding ε cyclase, isopentenyl pyrophosphate isomerase (IPP) and β-carotene hydroxylase as well as vectors containing the same and hosts transformed with said vectors. The present invention also provides a method for augmenting the accumulation of carotenoids and production of novel and rare carotenoids. The present invention provides methods for controlling the ratio of various carotenoids in a host. Additionally, the present invention provides a method for screening for eukaryotic genes encoding enzymes of carotenoid biosynthesis and metabolism.

2. Discussion of the Background

Carotenoid pigments with cyclic endgroups are essential components of the photosynthetic apparatus in oxygenic photosynthetic organisms (e.g., cyanobacteria, algae and plants; Goodwin, 1980). The symmetrical bicyclic yellow carotenoid pigment β-carotene (or, in rare cases, the asymmetrical bicyclic α-carotene) is intimately associated with the photosynthetic reaction centers and plays a vital role in protecting against potentially lethal photooxidative damage (Koyama, 1991). β-carotene and other carotenoids derived from it or from α-carotene also serve as light-harvesting pigments (Siefermann-Harms, 1987), are involved in the thermal dissipation of excess light energy captured by the light-harvesting antenna (Demmig-Adams & Adams, 1992), provide substrate for the biosynthesis of the plant growth regulator abscisic acid (Rock & Zeevaart, 1991; Parry & Horgan, 1992), and are precursors of vitamin A in human and animal diets (Krinsky, 1987). Plants also exploit carotenoids as coloring agents in flowers and fruits to attract pollinators and agents of seed dispersal (Goodwin, 1980). The color provided by carotenoids is also of agronomic value in a number of important crops. Carotenoids are currently harvested from plants for use as pigments in food and feed.

The probable pathway for formation of cyclic carotenoids in plants, algae and cyanobacteria is illustrated in FIG. 1. Two types of cyclic endgroups are commonly found in higher plant carotenoids, these are referred to as the β and ε cyclic endgroups (FIG. 3.; the acyclic endgroup is referred to as the Ψ or psi endgroup). These cyclic endgroups differ only in the position of the double bond in the ring. Carotenoids with two β rings are ubiquitous, and those with one β and one ε ring are common, but carotenoids with two ε rings are rarely detected. β-Carotene (FIG. 1) has two β endgroups and is a symmetrical compound that is the precursor of a number of other important plant carotenoids such as zeaxanthin and violaxanthin (FIG. 2).

Carotenoid enzymes have previously been isolated from a variety of sources including bacteria (Armstrong et al., 1989, Mol. Gen. Genet. 216, 254–268; Misawa et al., 1990, J. Bacteriol., 172, 6704–12), fungi (Schmidhauser et al., 1990, Mol. Cell. Biol. 10, 5064–70), cyanobacteria (Chamovitz et al., 1990, Z. Naturforsch, 45c, 482–86) and higher plants (Bartley et al., Proc. Natl. Acad. Sci USA 88, 6532–36; Martinez-Ferez & Vioque, 1992, Plant Mol. Biol. 18, 981–83). Many of the isolated enzymes show a great diversity in function and inhibitory properties between sources. For example, phytoene desaturases from Synechococcus and higher plants carry out a two-step desaturation to yield ζ-carotene as a reaction product; whereas the same enzyme from Erwinia introduces four double bonds forming lycopene. Similarity of the amino acid sequences are very low for bacterial versus plant enzymes. Therefore, even with a gene in hand from one source, it is difficult to screen for a gene with similar function in another source. In particular, the sequence similarity between prokaryotic and eukaryotic genes is quite low.

Further, the mechanism of gene expression in prokaryotes and eukaryotes appears to differ sufficiently such that one can not expect that an isolated eukaryotic gene will be properly expressed in a prokaryotic host.

The difficulties in isolating related genes is exemplified by recent efforts to isolated the enzyme which catalyzes the formation of β-carotene from the acyclic precursor lycopene. Although this enzyme had been isolated in a prokaryote, it had not been isolated from any photosynthetic organism nor had the corresponding genes been identified and sequenced or the cofactor requirements established. The isolation and characterization of the enzyme catalyzing formation of β-carotene in the cyanobacterium Synechococcus PCC7942 was described by the present inventors and others (Cunningham et al., 1993 and 1994).

The need remains for the isolation of eukaryotic genes involved in the carotenoid biosynthetic pathway, including a gene encoding an ε cyclase, IPP isomerase and β-carotene hydroxylase. There remains a need for methods to enhance the production of carotenoids. There also remains a need in the art for methods for screening for eukaryotic genes encoding enzymes of carotenoid biosynthesis and metabolism.

SUMMARY OF THE INVENTION

Accordingly, a first object of this invention is to provide isolated eukaryotic genes which encode enzymes involved in carotenoid biosynthesis; in particular, ε cyclase, IPP isomerase and β-carotene hydroxylase.

A second object of this invention is to provide eukaryotic genes which encode enzymes which produce novel carotenoids.

A third object of the present invention is to provide vectors containing said genes.

A fourth object of the present invention is to provide hosts transformed with said vectors.

Another object of the present invention is to provide hosts which accumulates novel or rare carotenoids or which overexpress known carotenoids.

Another object of the present invention is to provide hosts with inhibited carotenoid production.

Another object of this invention is to secure the expression of eukaryotic carotenoid-related genes in a recombinant prokaryotic host.

A final object of the present invention is to provide a method for screening for eukaryotic genes which encode enzymes involved in carotenoid biosynthesis and metabolism.

These and other objects of the present invention have been realized by the present inventors as described below.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a DNA sequence and the predicted amino acid sequence of ε cyclase isolated from A. thaliana (SEQ ID NOS: 1 and 2). These sequences were deposited under Genbank accession number U50738. This cDNA is incorporated into the plasmid pATeps.

FIG. 5 is a DNA sequence encoding the β-carotene hydroxylase isolated from A. thaliana (SEQ ID NO: 3). This cDNA is incorporated into the plasmid pATOHB.

FIG. 6 is an alignment of the predicted amino acid sequences of A. thaliana β-carotene hydroxylase (SEQ ID NO: 4) with the bacterial enzymes from Alicalgenes sp. (SEQ ID NO: 5) (Genbank D58422), Erwinia herbicola Eho10 (SEQ ID NO.: 6) (GenBank M872280), Erwinia uredovora (SEQ ID NO.: 7) (GenBank D90087) and Agrobacterium aurianticum (SEQ ID NO.: 8) (GenBank D58420). A consensus sequence is also shown. Consensus is identical for all five genes where a capital letter appears. A lowercase letter indicates that three of five, including A. thaliana, have the identical residue. TM; transmembrane FIG. 7 is a DNA sequence of a cDNA encoding an IPP isomerase isolated from A. thaliana (SEQ ID NO: 9). This cDNA is incorporated into the plasmid pATDP5.

FIG. 8 is a DNA sequence of a second cDNA encoding another IPP isomerase isolated from A. thaliana (SEQ ID NO: 10). This cDNA is incorporated into the plasmid pATDP7.

FIG. 9 is a DNA sequence of a cDNA encoding an IPP isomerase isolated from Haematococcus pluvialis (SEQ ID NO: 11). This cDNA is incorporated into the plasmid pHP04.

FIG. 10 is a DNA sequence of a second cDNA encoding another IPP isomerase isolated from Haematococcus pluvialis (SEQ ID NO: 12). This cDNA is incorporated into the plasmid pHP05.

FIG. 11 is an alignment of the predicted amino acid sequences of the IPP isomerase isolated from A. thaliana (SEQ ID NO.: 16 and 18), H. pluvialis (SEQ ID NOS.: 14 and 15), Clarkia breweri (SEQ ID NO.: 17) (See, Blanc & Pichersky, Plant Physiol. (1995) 108:855; Genbank accession no. X82627) and Saccharomyces cerevisiae (SEQ ID NO.: 19) (Genbank accession no. J05090).

FIG. 12 is a DNA sequence of the cDNA encoding an IPP-isomerase isolated from marigold (SEQ ID NO: 13). This cDNA is incorporated into the plasmid pPMDP1. xxx's denote a region not yet sequenced at the time when this application was prepared.

FIG. 13 is an alignment of the consensus sequence of 4 plant β-cyclases (SEQ ID NO.: 20) with the A. thaliana ε-cyclase (SEQ ID NO.: 21). A capital letter in the plant β consensus is used where all 4 β cyclase genes predict the same amino acid residue in this position. A small letter indicates that an identical residue was found in 3 of the 4. Dashes indicate that the amino acid residue was not conserved and dots in the sequence denote a gap. A consensus for the aligned sequences is given, in capital letters below the alignment, where the β and ε cyclase have the same amino acid residue. Arrows indicate some of the conserved amino acids that will be used as junction sites for construction of chimeric cyclases with novel enzymatic activities. Several regions of interest including a sequence signature indicative of a dinucleotide-binding motif and 2 predicted transmembrane (TM) helical regions are indicated below the alignment and are underlined.

DESCRIPTION OF THE PREFERRED EMBODIMENTS

Isolated Eukaryotic Genes which Encode Enzymes Involved in Carotenoid Iosynthesis The present inventors have now isolated eukaryotic genes encoding ε cyclase and β-carotene hydroxylase from A. thaliana and IPP isomerases from several sources.

The present inventors have now isolated the eukaryotic gene encoding the enzyme IPP isomerase which catalyzes the conversion of isopentenyl pyrophosphate (IPP) to dimethylallyl pyrophosphate (DMAPP). IPP isomerases were isolated from A. thaliana, H. pluvialis and marigold.

Alignments of these are shown in FIG. 11 (excluding the marigold sequence). Plasmids containing these genes were deposited with the American Type Culture Collection, 12301 Parklawn Drive, Rockville Md. 20852 on Mar. 4, 1996 under ATCC accession numbers 98000 (pHP05—H. pluvialis); 98001 (pMDP1—marigold); 98002 (pATDP7—H. pluvialis) and 98004 (pHP04—H. pluvialis).

The present inventors have also isolated the gene encoding the enzyme, ε cyclase, which is responsible for the formation of ε endgroups in carotenoids. A gene encoding an e cyclase from any organism has not heretofore been described. The A. thaliana ε cyclase adds an ε-ring to only one end of the symmetrical lycopene while the related β-cyclase adds a ring at both ends. The DNA of the present invention is shown in FIG. 4 and SEQ ID NO: 1. A plasmid containing this gene was deposited with the American Type Culture Collection, 12301 Parklawn Drive, Rockville Md. 20852 on Mar. 4, 1996 under ATCC accession number 98005 (pATeps—A. thaliana).

The present inventors have also isolated the gene encoding the enzyme, β-carotene hydroxylase, which is responsible for hydroxylating the β endgroup in carotenoids. The DNA of the present invention is shown in SEQ ID NO: 3 and FIG. 5. The full length gene product hydroxylates both end groups of β-carotene as do products of genes which encode proteins truncated by up to 50 amino acids from the N-terminus. Products of genes which encode proteins truncated between about 60–110 amino acids from the N-terminus preferentially hydroxylates only one ring. A plasmid containing this gene was deposited with the American Type Culture Collection, 12301 Parklawn Drive, Rockville Md. 20852 on Mar. 4, 1996 under ATCC accession number 98003 (pATOHB—*A. thaliana*).

Eukaryotic Genes which Encode Enzymes which Produce Novel or Rare Carotenoids

Figure 1:
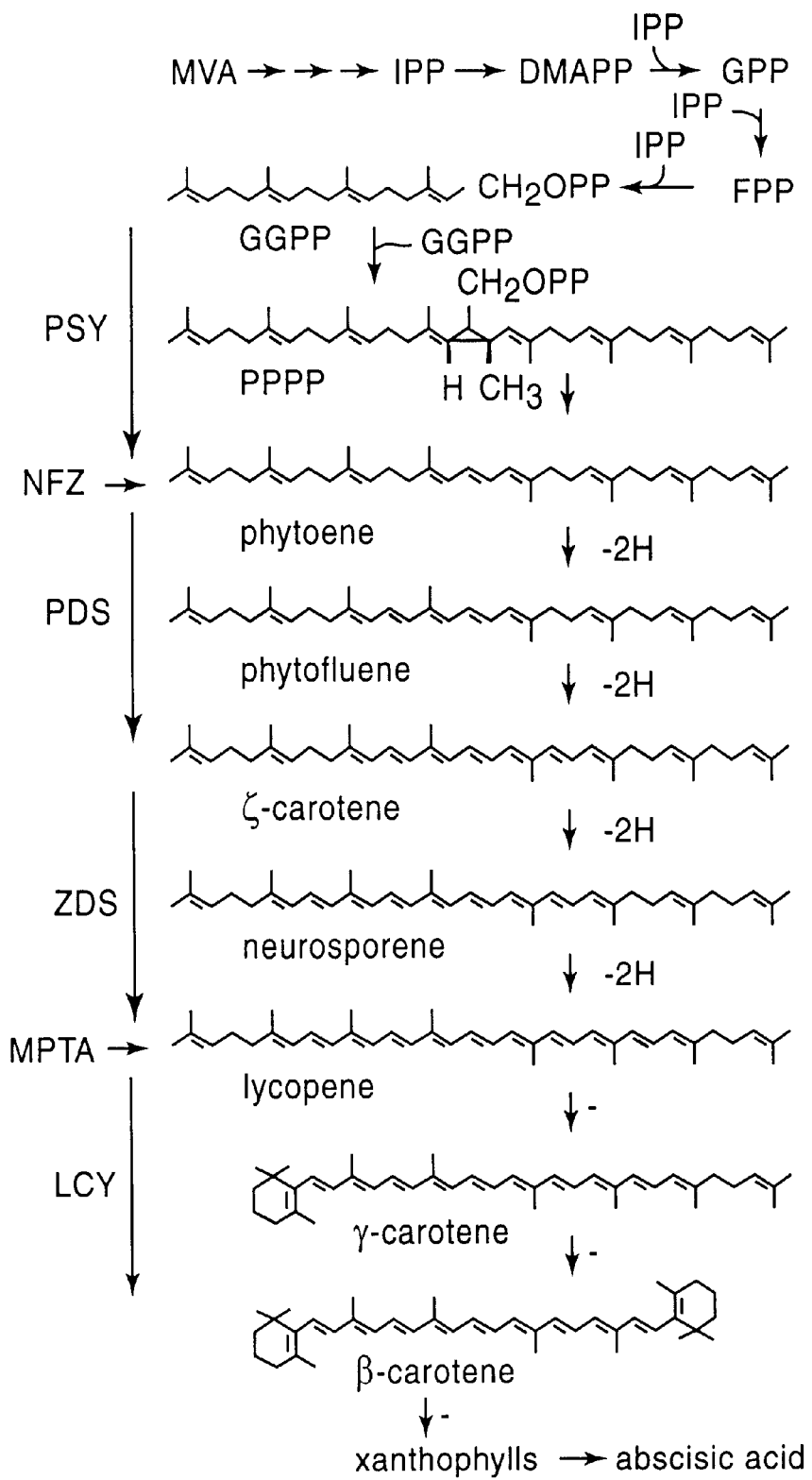
FIG. 1 is a schematic representation of the pathway of β-carotene biosynthesis in cyanobacteria, algae and plants. The enzymes catalyzing various steps are indicated at the left. Target sites of the bleaching herbicides NFZ and MPTA are also indicated at the left. Abbreviations: DMAPP, dimethylallyl pyrophosphate; FPP, farnesyl pyrophosphate; GGPP, geranylgeranyl pyrophosphate; GPP, geranyl pyrophosphate; IPP, isopentenyl pyrophosphate; LCY, lycopene cyclase; MVA, mevalonic acid; MPTA, 2-(4-methylphenoxy)triethylamine hydrochloride; NFZ, norflurazon; PDS, phytoene desaturase; PSY, phytoene synthase; ZDS, ζ-carotene desaturase; PPPP, prephytoene pyrophosphate.
Figure 2:
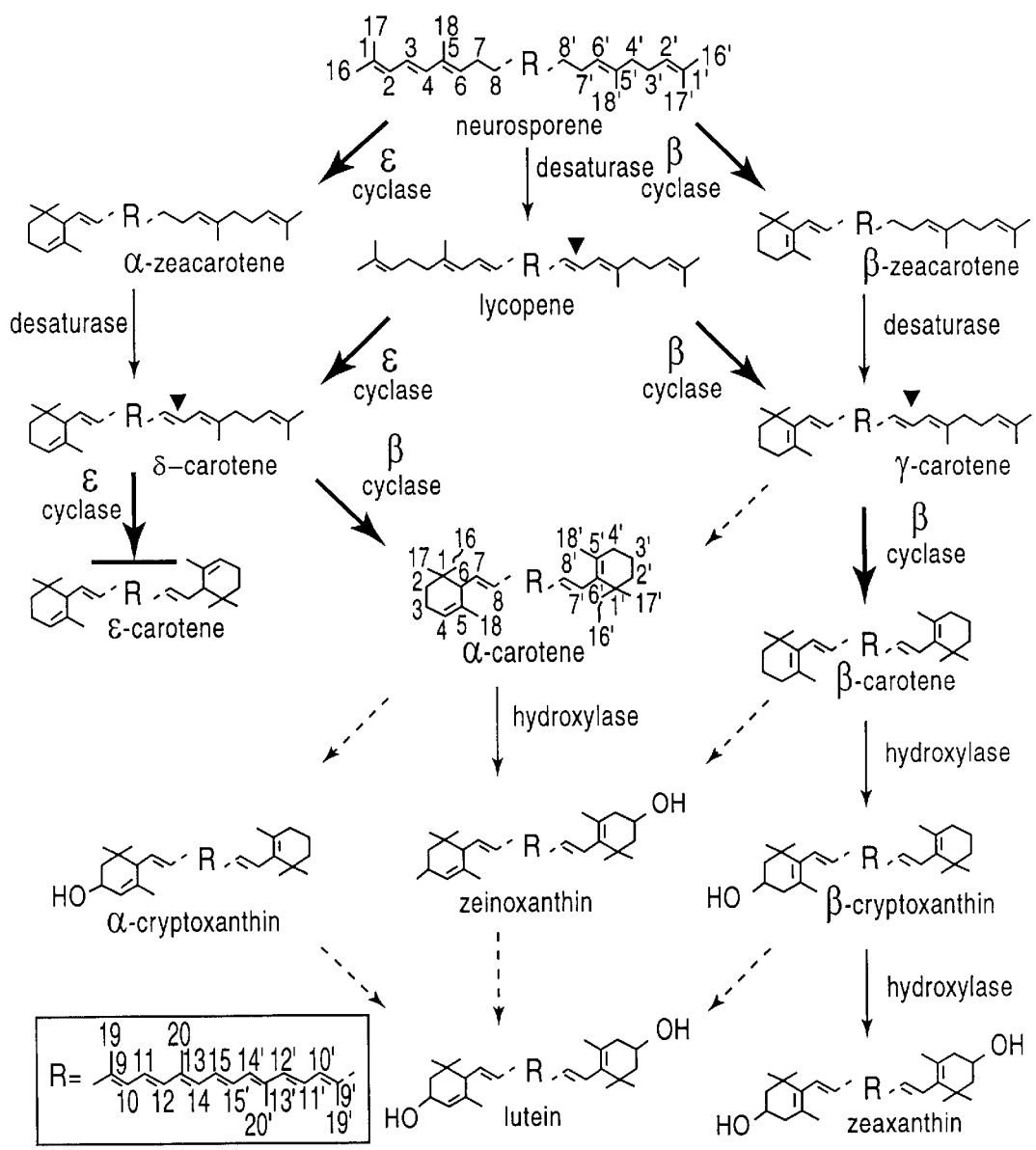
FIG. 2 depicts possible routes of synthesis of cyclic carotenoids and common plant and algal xanthophylls (oxycarotenoids) from neurosporene. Demonstrated activities of the β- and ε-cyclase enzymes of A. thalana are indicated by bold arrows labelled with β or ε respectively. A bar below the arrow leading to ε-carotene indicates that the enzymatic activity was examined but no product was detected. The steps marked by an arrow with a dotted line have not been specifically examined. Conventional numbering of the carbon atoms is given for neurosporene and α-carotene. Inverted triangles (▼) mark positions of the double bonds introduced as a consequence of the desaturation reactions.
Figure 3:
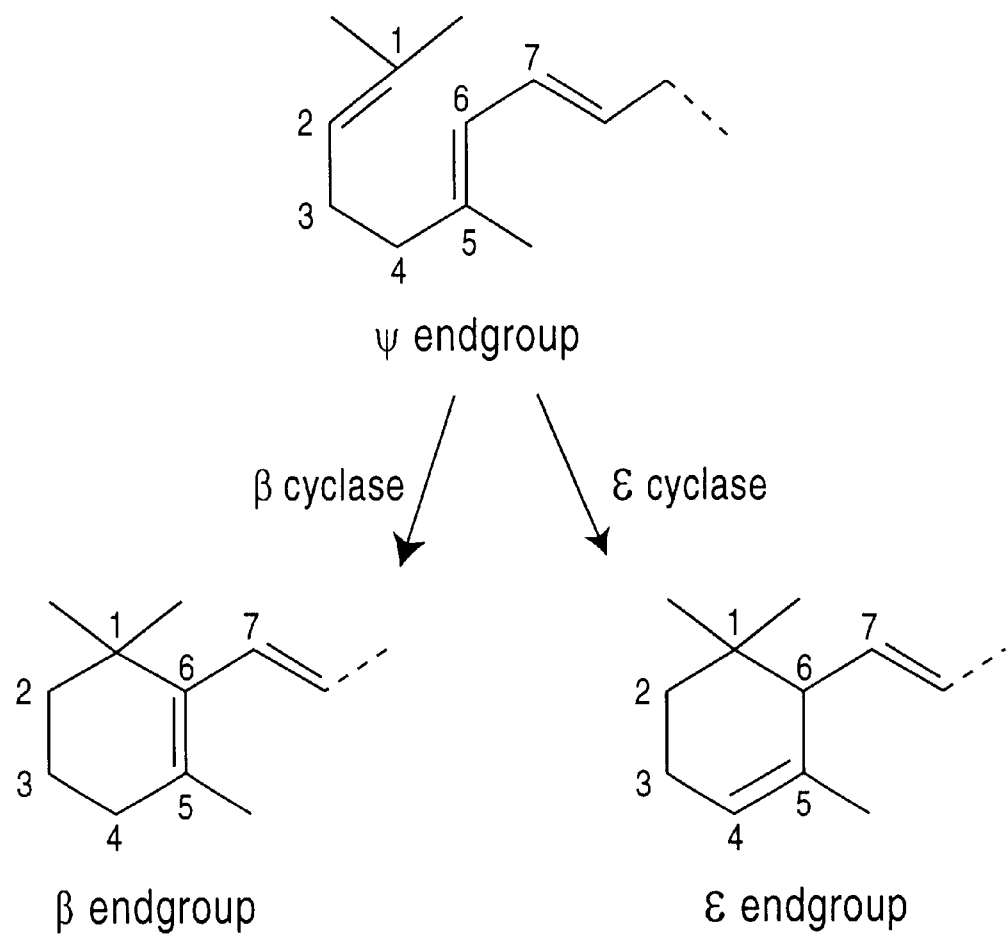
FIG. 3 depicts the carotene endgroups which are found in plants.

The present invention also relates to novel enzymes which can transform known carotenoids into novel or rare products. That is, currently ε-carotene (see FIG. 2) and γ-carotene can only be isolated in minor amounts. As described below, an enzyme can be produced which would transform lycopene to γ-carotene and lycopene to ε-carotene. With these products in hand, bulk synthesis of other carotenoids derived from them are possible. For example, ε-carotene can be hydroxylated to form an isomer of lutein (1 ε- and 1 β-ring) and zeaxanthin (2 β-rings) where both endgroups are, instead, ε-rings.

The eukaryotic genes in the carotenoid biosynthetic pathway differ from their prokaryotic counterparts in their 5' region. As used herein, the 5' region is the region of eukaryotic DNA which precedes the initiation codon of the counterpart gene in prokaryotic DNA. That is, when the consensus areas of eukaryotic and prokaryotic genes are aligned, the eukaryotic genes contain additional coding sequences upstream of the prokaryotic initiation codon.

The present inventors have found that the amount of the 5' region present can alter the activity of the eukaryotic enzyme. Instead of diminishing activity, truncating the 5' region of the eukaryotic gene results in an enzyme with a different specificity. Thus, the present invention relates to enzymes which are truncated to within 0–50, preferably 0–25, codons of the 5' initiation codon of their prokaryotic counterparts as determined by alignment maps.

For example, as discussed above, when the gene encoding *A. thaliana* β-carotene hydroxylase was truncated, the resulting enzyme catalyzed the formation of β-cryptoxanthin as major product and zeaxanthin as minor product; in contrast to its normal production of zeaxanthin.

In addition to novel enzymes produced by truncating the 5' region of known enzymes, novel enzymes which can participate in the formation of novel carotenoids can be formed by replacing portions of one gene with an analogous sequence from a structurally related gene. For example, β-cyclase and ε-cyclase are structurally related (see FIG. 13). By replacing a portion of ε-lycopene cyclase with the analogous portion of ε-cyclase, an enzyme which produces γ-carotene will be produced (1 endgroup). Further, by replacing a portion of the ε-lycopene cyclase with the analogous portion of β-cyclase, an enzyme which produces ε-carotene will be produced (ε-cyclase normally produces a compound with 1 ε-endgroup (δ-carotene) not 2). Similarly, β-hydroxylase could be modified to produce enzymes of novel function by creation of hybrids with ε-hydroxylase.

Vectors

The genes encoding the carotenoid enzymes as described above, when cloned into a suitable expression vector, can be used to overexpress these enzymes in a plant expression system or to inhibit the expression of these enzymes. For example, a vector containing the gene encoding ε-cyclase can be used to increase the amount of α-carotene in an organism and thereby alter the nutritional value, pharmacology and visual appearance value of the organism.

In a preferred embodiment, the vectors of the present invention contain a DNA encoding an eukaryotic IPP isomerase upstream of a DNA encoding a second eukaryotic carotenoid enzyme. The inventors have discovered that inclusion of an IPP isomerase gene increases the supply of substrate for the carotenoid pathway; thereby enhancing the production of carotenoid endproducts. This is apparent from the much deeper pigmentation in carotenoid-accumulating colonies of *E. coli* which also contain one of the aforementioned IPP isomerase genes when compared to colonies that lack this additional IPP isomerase gene. Similarly, a vector comprising an IPP isomerase gene can be used to enhance production of any secondary metabolite of dimethylallyl pyrophosphate (such as isoprenoids, steroids, carotenoids, etc.).

Alternatively, an anti-sense strand of one of the above genes can be inserted into a vector. For example, the ε-cyclase gene can be inserted into a vector and incorporated into the genomic DNA of a host, thereby inhibiting the synthesis of ε,β carotenoids (lutein and α-carotene) and enhancing the synthesis of β,β carotenoids (zeaxanthin and β-carotene).

Suitable vectors according to the present invention comprise a eukaryotic gene encoding an enzyme involved in carotenoid biosynthesis or metabolism and a suitable promoter for the host can be constructed using techniques well known in the art (for example Sambrook et al., *Molecular Cloning A Laboratory Manual*, Cold Spring Harbor Laboratory, Cold Spring Harbor, N.Y., 1989).

Suitable vectors for eukaryotic expression in plants are described in Frey et al., Plant J. (1995) 8(5):693 and Misawa et al, 1994a; incorporated herein by reference.

Suitable vectors for prokaryotic expression include pACYC184, pUC119, and pBR322 (available from New England BioLabs, Beverly, Mass.) and pTreHis (Invitrogen) and pET28 (Novagene) and derivatives thereof.

The vectors of the present invention can additionally contain regulatory elements such as promoters, repressors selectable markers such as antibiotic resistance genes, etc.

Hosts

Host systems according to the present invention can comprise any organism that already produces carotenoids or which has been genetically modified to produce carotenoids. The IPP isomerase genes are more broadly applicable for enhancing production of any product dependent on DMAPP as a precursor.

Organisms which already produce carotenoids include plants, algae, some yeasts, fungi and cyanobacteria and other photosynthetic bacteria. Transformation of these hosts with vectors according to the present invention can be done using standard techniques such as those described in Misawa et al., (1990); Hundle et al., (1993); Hundle et al., 1991); Misawa et al., (1990); Sandmann (1989); and Schnurr et al., (1991); all incorporated herein by reference.

Alternatively, transgenic organisms can be constructed which include the DNA sequences of the present invention (Bird et al, 1991; Bramley et al, 1992; Misawa et al, 1994a; Misawa et al, 1994b; Cunningham et al, 1993). The incorporation of these sequences can allow the controlling of carotenoid biosynthesis, content, or composition in the host cell. These transgenic systems can be constructed to incorporate sequences which allow over-expression of the carotenoid genes of the present invention. Transgenic systems can also be constructed containing antisense expression of the DNA sequences of the present invention. Such antisense expression would result in the accumulation of the substrates of the substrates of the enzyme encoded by the sense strand.

A Method for Screening for Eukaryotic Genes which Encode Enzymes Involved in Carotenoid Biosynthesis The method of the present invention comprises transforming a prokaryotic host with a DNA which may contain a eukaryotic or prokaryotic carotenoid biosynthetic gene; culturing said transformed host to obtain colonies; and screening for colonies exhibiting a different color than colonies of the untransformed host.

Suitable hosts include *E. coli*, cyanobacteria such as Synechococcus and Synechocystis, alga and plant cells. *E. coli* are preferred.

In a preferred embodiment, the above "color complementation test" can be enhanced by using mutants which are either (1) deficient in at least one carotenoid biosynthetic gene or (2) overexpress at least one carotenoid biosynthetic gene. In either case, such mutants will accumulate carotenoid precursors.

Prokaryotic and eukaryotic DNA libraries can be screened in total for the presence of genes of carotenoid biosynthesis, metabolism and degradation. Preferred organisms to be screened include photosynthetic organisms.

*E. coli* can be transformed with these eukaryotic cDNA libraries using conventional methods such as those described in Sambrook et al, 1989 and according to protocols described by the venders of the cloning vectors.

For example, the cDNA libraries in bacteriophage vectors such as lambdaZAP (Stratagene) or lambdaZIPOLOX (Gibco BRL) can be excised en masse and used to transform *E.coli* can be inserted into suitable vectors and these vectors can the be used to transform *E. coli*. Suitable vectors include pACYC184, pUC119, pBR322 (available from New England BioLabs, Beverly, Mass.). pACYC is preferred.

Transformed *E. coli* can be cultured using conventional techniques. The culture broth preferably contains antibiotics to select and maintain plasmids. Suitable antibiotics include penicillin, ampicillin, chloramphenicol, etc. Culturing is typically conducted at 20–40° C., preferably at room temperature (20–25° C.), for 12 hours to 7 days.

Cultures are plated and the plates are screened visually for colonies with a different color than the colonies of the untransformed host *E. coli*. For example, *E. coli* transformed with the plasmid, pAC-BETA (described below), produce yellow colonies that accumulate β-carotene. After transformation with a cDNA library, colonies which contain a different hue than those formed by *E. coli*/pAC-BETA would be expected to contain enzymes which modify the structure or degree of expression of β-carotene. Similar standards can be engineered which overexpress earlier products in carotenoid biosynthesis, such as lycopene, γ-carotene, etc.

Having generally described this invention, a further understanding can be obtained by reference to certain specific examples which are provided herein for purposes of illustration only and are not intended to be limiting unless otherwise specified.

EXAMPLE

I. Isolation of B-carotene Hydroxylase

Plasmid Construction

An 8.6 kb BglII fragment containing the carotenoid biosynthetic genes of *Erwinia herbicola* was first cloned in the BamHI site of plasmid vector pACYC184 (chloramphenicol resistant), and then a 1.1 kb BamHI fragment containing the β-carotene hydroxylase (CrtZ) was deleted. The resulting plasmid, pAC-BETA, contains all the genes for the formation of β-carotene. *E.coli* strains containing this plasmid accumulate β-carotene and form yellow colonies (Cunningham et al., 1994).

A full length gene encoding IPP isomerase of *Haematococcus pluvialis* (HP04) was first cut out with BamHI-KpnI from pBluescript SK+, and then cloned into a pTrcHisA vector with high-level expression from the trc promoter (Invitrogen Inc.). A fragment containing the IPP isomerase and trc promoter was excised with EcoRV-KpnI and cloned in HindIII site of pAC-BETA. *E.coli* cells transformed with this new plasmid pAC-BETA-04 form orange (deep yellow) colonies on LB plates and accumulate more β-carotene than cells that contain PAC-BETA.

Screening of the Arabidopsis cDNA Library

Several λ cDNA expression libraries of Arabidopsis were obtained from the Arabidopsis Biological Resource Center (Ohio State University, Columbus, Ohio) (Kieber et al., 1993). The λ cDNA libraries were excised in vivo using Stratagene's ExAssist SOLR system to produce a phagemid cDNA library wherein each clone also contained an amphicillin.

*E.coli* strain DH10BZIP was chosen as the host cells for the screening and pigment production. DH10B cells were transformed with plasmid pAC-BETA-04 and were plated on LB agar plates containing chloramphenicol at 50 μg/ml (from United States Biochemical Corporation). The phagemid Arabidopsis cDNA library was then introduced into DH10B cells already containing pAC-BETA-04. Transformed cells containing both pAC-BETA-04 and Arabidopsis cDNA were selected on chloramphenicol plus ampicillin (150 μg/ml) agar plates. Maximum color development occurred after 5 days incubation at room temperature, and lighter yellow colonies were selected. Selected colonies were inoculated into 3 ml liquid LB medium containing ampicillin and chloramphenicol, and cultures were incubated. Cells were then pelleted and extracted in 80 μl 100% acetone in microfuge tubes. After centrifugation, pigmented supernatant was spotted on silica gel thin-layer chromatography (TLC) plates, and developed with a hexane; ether (1:1) solvent system. β-carotene hydroxylase clones were identified based on the appearance of zeaxanthin on TLC plate.

Subcloning and Sequencing

The β-carotene hydroxylase cDNA was isolated by standard procedures (Sambrook et al., 1989). Restriction maps showed that three independent inserts (1.9 kb, 0.9 kb and 0.8 kb) existed in the cDNA. To determine which cDNA insert confers the β-carotene hydroxylase activity, plasmid DNA was digested with NotI (a site in the adaptor of the cDNA library) and three inserts were subcloned into NotI site of SK vectors. These subclones were used to transform *E. coli* cells containing pAC-BETA-04 again to test the hydroxylase activity. A fragment of 0.95 kb, later shown to contain the hydroxylase gene, was also blunt-ended and cloned into pTrcHis A,B,C vectors. To remove the N terminal sequence, a restriction site (BglII) was used that lies just before the conserved sequence with bacterial genes. A BglII-XhoI fragment was directionally cloned in BamHI-XhoI digested trc vectors. Functional clones were identified by the color complementation test. A β-carotene hydroxylase enzyme produces a colony with a lighter yellow color than is found in cells containing pAC-BETA-04 alone.

Arabidopsis β-carotene hydroxylase was sequenced completely on both strands on an automatic sequencer (Applied Biosystems, Model 373A, Version 2.0.1S).

Pigment Analysis

A single colony was used to inoculate 50 ml of LB containing ampicillin and chloramphenicol in a 250-ml flask. Cultures were incubated at 28° C. for 36 hours with gentle shaking, and then harvested at 5000 rpm in an SS-34 rotor. The cells were washed once with distilled $H_2O$ and resuspended with 0.5 ml of water. The extraction procedures and HPLC were essentially as described previously (Cunningham et al, 1994).

II. Isolation of ε Cyclase Plasmid Construction

Construction of Plasmids pAC-LYC, PAC-NEUR, and pAC-ZETA is described in Cunningham et al., (1994). In brief, the appropriate carotenoid biosynthetic genes from *Erwinia herbicola, Rhodobacter capsulatus,* and Synechococcus sp. strain PCC7942 were cloned in the plasmid vector pACYC184 (New England BioLabs, Beverly, Mass.). Cultures of *E. coli* containing the plasmids pAC-ZETA, pAC-NEUR, and pAC-LYC, accumulate ζ-carotene, neurosporene, and lycopene, respectively. The plasmid PAC-ZETA was constructed as follows: an 8.6-kb BglII fragment containing the carotenoid biosynthetic genes of *E. herbicola* (GenBank M87280; Hundle et al., 1991) was obtained after partial digestion of plasmid pPL376 (Perry et al., 1986; Tuveson et al., 1986) and cloned in the BamHI site of pACYC184 to give the plasmid pAC-EHER. Deletion of adjacent 0.8- and 1.1-kb BamHI-BamHI fragments (deletion Z in Cunningham et al., 1994), and of a 1.1 kB SalI-SalI fragment (deletion X) served to remove most of the coding regions for the *E. herbicola* β-carotene hydroxylase (crt gene) and zeaxanthin glucosyltransferase (crtx gene), respectively. The resulting plasmid, pAC-BETA, retains functional genes for geranylgeranyl pyrophosphate synthase (crtE), phytoene synthase (crtB), phytoene desaturase (crtI), and lycopene cyclase (crtY). Cells of *E. coli* containing this plasmid form yellow colonies and accumulate β-carotene. A plasmid containing both the ε- and β-cyclase cDNAs of *A. thaliana* was constructed by excising the ε cyclase in clone y2 as a PvuI-PvuII fragment and ligating this piece in the SnaBI site of a plasmid (pSPORT 1 from GIBCO-BRL) that already contained the β cyclase.

Organisms and Growth Conditions

*E. coli* strains TOP10 and TOP10 F' (obtained from Invitrogen Corporation, San Diego, Calif.) and XL1-Blue (Stratagene) were grown in Luria-Bertani (LB) medium (Sambrook et al., 1989) at 37° C. in darkness on a platform shaker at 225 cycles per min. Media components were from Difco (yeast extract and tryptone) or Sigma (NaCl). Ampicillin at 150 µg/mL and/or chloramphenicol at 50 µg/mL (both from United States Biochemical Corporation) were used, as appropriate, for selection and maintenance of plasmids.

Mass Excision and Color Complementation Screening of an *A. thaliana* cDNA Library A size-fractionated 1–2 kB cDNA library of *A. thaliana* in lambda ZAPII (Kieber et al., 1993) was obtained from the Arabidopsis Biological Resource Center at The Ohio State University (stock number CD4-14). Other size fractionated libraries were also obtained (stock numbers CD4-13, CD4-15, and CD4-16). An aliquot of each library was treated to cause a mass excision of the cDNAs and thereby produce a phagemid library according to the instructions provided by the supplier of the cloning vector (Stratagene; *E. coli* strain XL1-Blue and the helper phage R408 were used). The titre of the excised phagemid was determined and the library was introduced into a lycopene-accumulating strain of *E. coli* TOP10 F' (this strain contained the plasmid PAC-LYC) by incubation of the phagemid with the *E. coli* cells for 15 min at 37° C. Cells had been grown overnight at 30° C. in LB medium supplemented with 2% (w/v) maltose and 10 mM $MgSO_4$ (final concentration), and harvested in 1.5 ml microfuge tubes at a setting of 3 on an Eppendorf microfuge (5415C) for 10 min. The pellets were resuspended in 10 mM $MgSO_4$ to a volume equal to one-half that of the initial culture volume. Transformants were spread on large (150 mm diameter) LB agar petri plates containing antibiotics to provide for selection of cDNA clones (ampicillin) and maintenance of pAC-LYC (chloramphenicol). Approximately 10,000 colony forming units were spread on each plate. Petri plates were incubated at 37° C. for 16 hr and then at room temperature for 2 to 7 days to allow maximum color development. Plates were screened visually with the aid of an illuminated 3× magnifier and a low power stage-dissecting microscope for the rare, pale pinkish-yellow to deep-yellow colonies that could be observed in the background of pink colonies. A colony color of yellow or pinkish-yellow was taken as presumptive evidence of a cyclization activity. These yellow colonies were collected with sterile toothpicks and used to inoculate 3ml of LB medium in culture tubes with overnight growth at 37° C. and shaking at 225 cycles/min. Cultures were split into two aliquots in microfuge tubes and harvested by centrifugation at a setting of 5 in an Eppendorf 5415C microfuge. After discarding the liquid, one pellet was frozen for later purification of plasmid DNA. To the second pellet was added 1.5 ml EtOH, and the pellet was resuspended by vortex mixing, and extraction was allowed to proceed in the dark for 15–30 min with occasional remixing. Insoluble materials were pelleted by centrifugation at maximum speed for 10 min in a microfuge. Absorption spectra of the supernatant fluids were recorded from 350–550 nm with a Perkin Elmer lambda six spectrophotometer.

Analysis of Isolated Clones

Eight of the yellow colonies contained β-carotene indicating that a single gene product catalyzes both cyclizations required to form the two β endgroups of the symmetrical β-carotene from the symmetrical precursor lycopene. One of the yellow colonies contained a pigment with the spectrum characteristic of δ-carotene, a monocyclic carotenoid with a single ε endgroup. Unlike the β cyclase, this ε cyclase appears unable to carry out a second cyclization at the other end of the molecule.

The observation that ε cyclase is unable to form two cyclic ε endgroups (e.g. the bicyclic ε-carotene) illuminates the mechanism by which plants can coordinate and control the flow of substrate into carotenoids derived from β-carotene versus those derived from α-carotene and also can prevent the formation of carotenoids with two ε endgroups.

The availability of the *A. thaliana* gene encoding the ε cyclase enables the directed manipulation of plant and algal species for modification of carotenoid content and composition. Through inactivation of the ε cyclase, whether at the gene level by deletion of the gene or by insertional inactivation or by reduction of the amount of enzyme formed (by such as antisense technology), one may increase the formation of β-carotene and other pigments derived from it. Since vitamin A is derived only from carotenoids with β endgroups, an enhancement of the production of β-carotene versus α-carotene may enhance nutritional value of crop plants. Reduction of carotenoids with ε endgroups may also be of value in modifying the color properties of crop plants and specific tissues of these plants. Alternatively, where production of α-carotene, or pigments such as lutein that are derived from α-carotene, is desirable, whether for the color properties, nutritional value or other reason, one may overexpress the ε cyclase or express it in specific tissues. Wherever agronomic value of a crop is related to pigmentation provided by carotenoid pigments the directed manipu lation of expression of the ε cyclase gene and/or production of the enzyme may be of commercial value.

The predicted amino acid sequence of the *A. thaliana* ε cyclase enzyme was determined. A comparison of the amino acid sequences of the β and ε cyclase enzymes of *Arabidopsis thaliana* (FIG. 13) as predicted by the DNA sequence of the respective genes (FIG. 4 for the ε cyclase cDNA sequence), indicates that these two enzymes have many regions of sequence similarity, but they are only about 37% identical overall at the amino acid level. The degree of sequence identity at the DNA base level, only about 50%, is sufficiently low such that we and others have been unable to detect this gene by hybridization using the β cyclase as a probe in DNA gel blot experiments.

REFERENCES

Bird et al, (1991) Biotechnology 9, 635–639.
Bishop et al., (1995) FEBS Lett. 367, 158–162.
Bramley, P. M. (1985) Adv. Lipid Res. 21, 243–279.
Bramley, P. M. (1992) Plant J. 2, 343–349.
Britton, G. (1988). Biosynthesis of carotenoids. In Plant Pigments, T. W. Goodwin, ed. (London: Academic Press), pp. 133–182.
Britton, G. (1979) Z. Naturforsch. Section C Biosci. 34, 979–985.
Britton, G. (1995) UV/Visible spectroscopy. In Carotenoids, Vol. IB: Spectroscopy, G. Britton, S. Liaaen-Jensen, H. P. Pfander, eds. (Basel: Birkhauser Verlag), pp. 13–62.
Bouvier et al., (1994) Plant J. 6, 45–54.
Cunningham et al., (1985) Photochem. Photobiol. 42: 295–307.
Cunningham et al., (1993) FEBS Lett. 328, 130–138.
Cunningham et al., (1994) Plant Cell 6, 1107–1121.
Davies, B. H. (1976). Carotenoids. In Chemistry and Biochemistry of Plant Pigments, Vol. 2, T. W. Goodwin, ed (New York: Academic Press), pp. 38–165.
Del Sal et al., (1988). Nucl. Acids Res. 16, 9878.
Demmig-Adams & Adams, (1992) Ann. Rev. Plant Physiol. Mol. Biol. 43, 599–626.
Enzell & Back, (1995) Mass spectrometry. In Carotenoids, Vol. IB: Spectroscopy, G. Britton, S. Liaaen-Jensen, H. P. Pfander, eds. (Basel: Birkhauser Verlag), pp. 261–320.
Frank & Cogdell (1993) Photochemistry and function of carotenoids in photosynthesis. In Carotenoids in Photosynthesis. A. Young and G. Britton, eds. (London: Chapman and Hall). pp. 253–326.
Goodwin, T. W. (1980). The Biochemistry of the Carotenoids. 2nd ed, Vol. 1 (London: Chapman and Hall.
Horvath et al., (1972) Phytochem. 11, 183–187.
Hugueney et al., (1995) Plant J. 8, 417–424.
Hundle et al., (1991) Photochem. Photobiol. 54, 89–93.
Hundle et al, (1993) FEBS Lett. 315, 329–334.
Jensen & Jensen, (1971) Methods Enzymol. 23, 586–602.
Kargl & Quackenbush, (1960) Archives Biochem. Biophys. 88, 59–63.
Kargl et al., (1960) Proc. Am. Hort. Soc. 75, 574–578.
Kieber et al., (1993) Cell 72, 427–441.
Koyama, Y. (1991) J. Photochem. Photobiol., B, 9, 265–80.
Krinsky, N. I. (1987) Medical uses of carotenoids. In Carotenoids, N. I. Krinsky, M. M. Mathews-Roth, and R. F. Taylor, eds. (New York: Plenum), pp. 195–206.

Kyte & Doolittle, (1982) J. Mol. Biol. 157, 105–132.
LaRossa & Schloss, (1984) J. Biol. Chem. 259, 8753–8757.
Misawa et al (1990) J. Bacteriol. 172:6704–6712.
Misawa et al., (1994a) Plant J. 6, 481–489.
Misawa et al., (1994b) J. Biochem, Tokyo, 116, 980–985.
Norris et al., (1995) Plant Cell 7, 2139–2149.
Parry & Hogan (1992) Planta 187:185–191.
Pecker et al., (1996) Submitted to Plant Mol. Biol.
Perry et al., (1986) J. Bacteriol. 168, 607–612.
Persson & Argos, (1994) J. Mol. Biol. 237, 182–192.
Plumley & Schmidt, (1987) Proc. Nat. Acad. Sci. USA 83, 146–150.
Plumley & Schmidt, (1995) Plant Cell 7, 689–704.
Rossmann et al., (1974) Nature 250, 194–199.
Rock & Zeevaart (1991) Proc. Nat. Acad. Sci. USA 88, 7496–7499.
Rost et al., (1995) Protein Science 4, 521–533.
Sambrook et al., (1989) Molecular Cloning: A Laboratory Manual, 2nd edition (Cold Spring Harbor, N.Y.: Cold Spring Harbor Laboratory Press).
Sancar, A. (1994) Biochemistry 33, 2–9.
Sander & Schneider, (1991) Proteins 9, 56–68.
Sandmann, G. (1989) CRC Press, Target Sites, 25–44.
Sandmann, G. (1994) Eur. J. Biochem. 223, 7–24.
Scolnik & Bartley, (1995) Plant Physiol. 108, 1342.
Schnurr et al (1991) FEMS Microb. Lett. 78:157.
Siefermann-Harms, D. (1987) Physiol. Plant. 69, 561–568.
Spurgeon & Porter, (1980). Biosynthesis of carotenoids. In Biochemistry of Isoprenoid Compounds, J. W. Porter, and S. L. Spurgeon, eds. (New York: Wiley), pp. 1–122.

Tomes, M. L. (1963) Bot. Gaz. 124, 180–185.
Tomes, M. L. (1967) Genetics 56, 227–232.
Tuveson et al., (1986) J. Bacteriol. 170, 4675–4680.
Van Beeumen et al., (1991) J. Biol. Chem. 266, 12921–12931.
Weedon & Moss, (1995) Structure and Nomenclature. In Carotenoids, Vol. IB: Spectroscopy, G. Britton, S. Liaaen-Jensen, H. P. Pfander, eds. (Basel: Birkhauser Verlag), pp. 27–70.
Wierenga et al., (1986) J. Mol. Biol. 187, 101–107.
Zechmeister, L. (1962) Cis-Trans Isomeric Carotenoids, Vitamins A and Arylpolyenes. Springer-Verlag, Vienna.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method of obtaining a compound derived from dimethylallyl pyrophosphate (DMAPP), wherein said compound derived from DMAPP is an isoprenoid, steroid, or carotenoid, the method comprising:

(a) inserting into a host cell a vector comprising a heterologous nucleic acid sequence, which encodes a protein having isopentenyl pyrophosphate (IPP) isomerase activity, wherein the heterologous nucleic acid sequence is operably linked to a promoter;

(b) expressing the heterologous nucleic acid sequence to produce the protein wherein the protein enhances the production of a compound derived from DMAPP relative to an untransformed host cell;

(c) observing the host cell for a color change caused by the enhanced production of a compound derived from DMAPP; and (d) recovering the compound derived from DMAPP from the host cell.

2. The method of claim 1, wherein the heterologous nucleic acid sequence has a sequence which encodes the amino acid sequence of SEQ ID NO: 14, 15, 16 or 18.

3. The method of claim 1, wherein the host cell is selected from the group consisting of a bacterial cell, an algal cell, a plant cell and a cyanobacterial cell.

4. The method of claim 1, wherein the host cell is a photosynthetic cell.

5. The method of claim 1, wherein the host cell is an *E. coli* cell.

6. A method of enhancing the production of a compound derived from DMAPP in a host cell, wherein said compound derived from DMAPP is an isoprenoid, steroid, or carotenoid, the method comprising:

(a) inserting into a host cell a vector comprising a heterologous nucleic acid sequence, which encodes a protein having isopentenyl pyrophosphate (IPP) isomerase activity, wherein the heterologous nucleic acid sequence is operably linked to a promoter;

(b) expressing the heterologous nucleic acid sequence to produce the protein wherein the protein enhances the production of a compound derived from DMAPP sufficiently to alter the visual appearance of the host cell by a color change relative to an untransformed host cell; and (c) observing the host cells into which the vector has been inserted for said color change.

7. The method of claim 6, wherein the heterologous nucleic acid sequence has a sequence which encodes the amino acid sequence of SEQ ID NO: 14, 15, 16 or 18.

8. The method of claim 6, wherein the host cell is selected from the group consisting of a bacterial cell, an algal cell, a plant cell and a cyanobacterial cell.

9. The method of claim 6, wherein the host cell is a photosynthetic cell.

10. The method of claim 6, wherein the host cell is an *E. coli* cell.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 1860 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 109..1680
      (D) OTHER INFORMATION: /product= "E-CYCLASE FROM A.
         THALIANA"

(xi) SEQUENCE DESCRIPTION: SEQ ID NO:1:

```
ACAAAAGGAA ATAATTAGAT TCCTCTTTCT GCTTGCTATA CCTTGATAGA ACAATATAAC         60

AATGGTGTAA GTCTTCTCGC TGTATTCGAA ATTATTTGGA GGAGGAAA ATG GAG TGT         117
                                                    Met Glu Cys
                                                     1

GTT GGG GCT AGG AAT TTC GCA GCA ATG GCG GTT TCA ACA TTT CCG TCA         165
Val Gly Ala Arg Asn Phe Ala Ala Met Ala Val Ser Thr Phe Pro Ser
     5                  10                  15

TGG AGT TGT CGA AGG AAA TTT CCA GTG GTT AAG AGA TAC AGC TAT AGG         213
Trp Ser Cys Arg Arg Lys Phe Pro Val Val Lys Arg Tyr Ser Tyr Arg
 20                  25                  30                  35

AAT ATT CGT TTC GGT TTG TGT AGT GTC AGA GCT AGC GGC GGC GGA AGT         261
Asn Ile Arg Phe Gly Leu Cys Ser Val Arg Ala Ser Gly Gly Gly Ser
                 40                  45                  50

TCC GGT AGT GAG AGT TGT GTA GCG GTG AGA GAA GAT TTC GCT GAC GAA         309
Ser Gly Ser Glu Ser Cys Val Ala Val Arg Glu Asp Phe Ala Asp Glu
             55                  60                  65

GAA GAT TTT GTG AAA GCT GGT GGT TCT GAG ATT CTA TTT GTT CAA ATG         357
Glu Asp Phe Val Lys Ala Gly Gly Ser Glu Ile Leu Phe Val Gln Met
         70                  75                  80

CAG CAG AAC AAA GAT ATG GAT GAA CAG TCT AAG CTT GTT GAT AAG TTG         405
Gln Gln Asn Lys Asp Met Asp Glu Gln Ser Lys Leu Val Asp Lys Leu
     85                  90                  95

CCT CCT ATA TCA ATT GGT GAT GGT GCT TTG GAT CAT GTG GTT ATT GGT         453
Pro Pro Ile Ser Ile Gly Asp Gly Ala Leu Asp His Val Val Ile Gly
100                 105                 110                 115

TGT GGT CCT GCT GGT TTA GCC TTG GCT GCA GAA TCA GCT AAG CTT GGA         501
Cys Gly Pro Ala Gly Leu Ala Leu Ala Ala Glu Ser Ala Lys Leu Gly
                120                 125                 130

TTA AAA GTT GGA CTC ATT GGT CCA GAT CTT CCT TTT ACT AAC AAT TAC         549
Leu Lys Val Gly Leu Ile Gly Pro Asp Leu Pro Phe Thr Asn Asn Tyr
            135                 140                 145

GGT GTT TGG GAA GAT GAA TTC AAT GAT CTT GGG CTG CAA AAA TGT ATT         597
Gly Val Trp Glu Asp Glu Phe Asn Asp Leu Gly Leu Gln Lys Cys Ile
        150                 155                 160

GAG CAT GTT TGG AGA GAG ACT ATT GTG TAT CTG GAT GAT GAC AAG CCT         645
Glu His Val Trp Arg Glu Thr Ile Val Tyr Leu Asp Asp Asp Lys Pro
    165                 170                 175

ATT ACC ATT GGC CGT GCT TAT GGA AGA GTT AGT CGA CGT TTG CTC CAT         693
Ile Thr Ile Gly Arg Ala Tyr Gly Arg Val Ser Arg Arg Leu Leu His
180                 185                 190                 195
```

```
GAG GAG CTT TTG AGG AGG TGT GTC GAG TCA GGT GTC TCG TAC CTT AGC       741
Glu Glu Leu Leu Arg Arg Cys Val Glu Ser Gly Val Ser Tyr Leu Ser
            200                 205                 210

TCG AAA GTT GAC AGC ATA ACA GAA GCT TCT GAT GGC CTT AGA CTT GTT       789
Ser Lys Val Asp Ser Ile Thr Glu Ala Ser Asp Gly Leu Arg Leu Val
            215                 220                 225

GCT TGT GAC GAC AAT AAC GTC ATT CCC TGC AGG CTT GCC ACT GTT GCT       837
Ala Cys Asp Asp Asn Asn Val Ile Pro Cys Arg Leu Ala Thr Val Ala
            230                 235                 240

TCT GGA GCA GCT TCG GGA AAG CTC TTG CAA TAC GAA GTT GGT GGA CCT       885
Ser Gly Ala Ala Ser Gly Lys Leu Leu Gln Tyr Glu Val Gly Gly Pro
            245                 250                 255

AGA GTC TGT GTG CAA ACT GCA TAC GGC GTG GAG GTT GAG GTG GAA AAT       933
Arg Val Cys Val Gln Thr Ala Tyr Gly Val Glu Val Glu Val Glu Asn
260                 265                 270                 275

AGT CCA TAT GAT CCA GAT CAA ATG GTT TTC ATG GAT TAC AGA GAT TAT       981
Ser Pro Tyr Asp Pro Asp Gln Met Val Phe Met Asp Tyr Arg Asp Tyr
            280                 285                 290

ACT AAC GAG AAA GTT CGG AGC TTA GAA GCT GAG TAT CCA ACG TTT CTG      1029
Thr Asn Glu Lys Val Arg Ser Leu Glu Ala Glu Tyr Pro Thr Phe Leu
            295                 300                 305

TAC GCC ATG CCT ATG ACA AAG TCA AGA CTC TTC TTC GAG GAG ACA TGT      1077
Tyr Ala Met Pro Met Thr Lys Ser Arg Leu Phe Phe Glu Glu Thr Cys
            310                 315                 320

TTG GCC TCA AAA GAT GTC ATG CCC TTT GAT TTG CTA AAA ACG AAG CTC      1125
Leu Ala Ser Lys Asp Val Met Pro Phe Asp Leu Leu Lys Thr Lys Leu
            325                 330                 335

ATG TTA AGA TTA GAT ACA CTC GGA ATT CGA ATT CTA AAG ACT TAC GAA      1173
Met Leu Arg Leu Asp Thr Leu Gly Ile Arg Ile Leu Lys Thr Tyr Glu
340                 345                 350                 355

GAG GAG TGG TCC TAT ATC CCA GTT GGT GGT TCC TTG CCA AAC ACC GAA      1221
Glu Glu Trp Ser Tyr Ile Pro Val Gly Gly Ser Leu Pro Asn Thr Glu
            360                 365                 370

CAA AAG AAT CTC GCC TTT GGT GCT GCC GCT AGC ATG GTA CAT CCC GCA      1269
Gln Lys Asn Leu Ala Phe Gly Ala Ala Ala Ser Met Val His Pro Ala
            375                 380                 385

ACA GGC TAT TCA GTT GTG AGA TCT TTG TCT GAA GCT CCA AAA TAT GCA      1317
Thr Gly Tyr Ser Val Val Arg Ser Leu Ser Glu Ala Pro Lys Tyr Ala
            390                 395                 400

TCA GTC ATC GCA GAG ATA CTA AGA GAA GAG ACT ACC AAA CAG ATC AAC      1365
Ser Val Ile Ala Glu Ile Leu Arg Glu Glu Thr Thr Lys Gln Ile Asn
            405                 410                 415

AGT AAT ATT TCA AGA CAA GCT TGG GAT ACT TTA TGG CCA CCA GAA AGG      1413
Ser Asn Ile Ser Arg Gln Ala Trp Asp Thr Leu Trp Pro Pro Glu Arg
420                 425                 430                 435

AAA AGA CAG AGA GCA TTC TTT CTC TTT GGT CTT GCA CTC ATA GTT CAA      1461
Lys Arg Gln Arg Ala Phe Phe Leu Phe Gly Leu Ala Leu Ile Val Gln
            440                 445                 450

TTC GAT ACC GAA GGC ATT AGA AGC TTC TTC CGT ACT TTC TTC CGC CTT      1509
Phe Asp Thr Glu Gly Ile Arg Ser Phe Phe Arg Thr Phe Phe Arg Leu
            455                 460                 465

CCA AAA TGG ATG TGG CAA GGG TTT CTA GGA TCA ACA TTA ACA TCA GGA      1557
Pro Lys Trp Met Trp Gln Gly Phe Leu Gly Ser Thr Leu Thr Ser Gly
            470                 475                 480

GAT CTC GTT CTC TTT GCT TTA TAC ATG TTC GTC ATT TCA CCA AAC AAT      1605
Asp Leu Val Leu Phe Ala Leu Tyr Met Phe Val Ile Ser Pro Asn Asn
            485                 490                 495

TTG AGA AAA GGT CTC ATC AAT CAT CTC ATC TCT GAT CCA ACC GGA GCA      1653
Leu Arg Lys Gly Leu Ile Asn His Leu Ile Ser Asp Pro Thr Gly Ala
```

```
500              505              510              515
ACC ATG ATA AAA ACC TAT CTC AAA GTA TGATTTACTT ATCAACTCTT           1700
Thr Met Ile Lys Thr Tyr Leu Lys Val
                520

AGGTTTGTGT ATATATATGT TGATTTATCT GAATAATCGA TCAAAGAATG GTATGTGGGT  1760

TACTAGGAAG TTGGAAACAA ACATGTATAG AATCTAAGGA GTGATCGAAA TGGAGATGGA  1820

AACGAAAAGA AAAAAATCAG TCTTTGTTTT GTGGTTAGTG                        1860
```

(2) INFORMATION FOR SEQ ID NO:2:

(i) SEQUENCE CHARACTERISTICS:
        (A) LENGTH: 524 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Cys Val Gly Ala Arg Asn Phe Ala Ala Met Ala Val Ser Thr
 1               5                  10                  15

Phe Pro Ser Trp Ser Cys Arg Arg Lys Phe Pro Val Val Lys Arg Tyr
            20                  25                  30

Ser Tyr Arg Asn Ile Arg Phe Gly Leu Cys Ser Val Arg Ala Ser Gly
        35                  40                  45

Gly Gly Ser Ser Gly Ser Glu Ser Cys Val Ala Val Arg Glu Asp Phe
    50                  55                  60

Ala Asp Glu Glu Asp Phe Val Lys Ala Gly Ser Glu Ile Leu Phe
65                  70                  75                  80

Val Gln Met Gln Gln Asn Lys Asp Met Asp Glu Gln Ser Lys Leu Val
                85                  90                  95

Asp Lys Leu Pro Pro Ile Ser Ile Gly Asp Gly Ala Leu Asp His Val
            100                 105                 110

Val Ile Gly Cys Gly Pro Ala Gly Leu Ala Leu Ala Ala Glu Ser Ala
        115                 120                 125

Lys Leu Gly Leu Lys Val Gly Leu Ile Gly Pro Asp Leu Pro Phe Thr
    130                 135                 140

Asn Asn Tyr Gly Val Trp Glu Asp Glu Phe Asn Asp Leu Gly Leu Gln
145                 150                 155                 160

Lys Cys Ile Glu His Val Trp Arg Glu Thr Ile Val Tyr Leu Asp Asp
                165                 170                 175

Asp Lys Pro Ile Thr Ile Gly Arg Ala Tyr Gly Arg Val Ser Arg Arg
            180                 185                 190

Leu Leu His Glu Glu Leu Leu Arg Arg Cys Val Glu Ser Gly Val Ser
        195                 200                 205

Tyr Leu Ser Ser Lys Val Asp Ser Ile Thr Glu Ala Ser Asp Gly Leu
    210                 215                 220

Arg Leu Val Ala Cys Asp Asp Asn Val Ile Pro Cys Arg Leu Ala
225                 230                 235                 240

Thr Val Ala Ser Gly Ala Ala Ser Gly Lys Leu Leu Gln Tyr Glu Val
                245                 250                 255

Gly Gly Pro Arg Val Cys Val Gln Thr Ala Tyr Gly Val Glu Val
            260                 265                 270

Val Glu Asn Ser Pro Tyr Asp Pro Asp Gln Met Val Phe Met Asp Tyr
        275                 280                 285

Arg Asp Tyr Thr Asn Glu Lys Val Arg Ser Leu Glu Ala Glu Tyr Pro
```

```
                290             295             300
Thr Phe Leu Tyr Ala Met Pro Met Thr Lys Ser Arg Leu Phe Phe Glu
305             310             315             320

Glu Thr Cys Leu Ala Ser Lys Asp Val Met Pro Phe Asp Leu Leu Lys
            325             330             335

Thr Lys Leu Met Leu Arg Leu Asp Thr Leu Gly Ile Arg Ile Leu Lys
            340             345             350

Thr Tyr Glu Glu Trp Ser Tyr Ile Pro Val Gly Gly Ser Leu Pro
        355             360             365

Asn Thr Glu Gln Lys Asn Leu Ala Phe Gly Ala Ala Ser Met Val
        370             375             380

His Pro Ala Thr Gly Tyr Ser Val Val Arg Ser Leu Ser Glu Ala Pro
385             390             395             400

Lys Tyr Ala Ser Val Ile Ala Glu Ile Leu Arg Glu Glu Thr Thr Lys
            405             410             415

Gln Ile Asn Ser Asn Ile Ser Arg Gln Ala Trp Asp Thr Leu Trp Pro
            420             425             430

Pro Glu Arg Lys Arg Gln Arg Ala Phe Phe Leu Phe Gly Leu Ala Leu
            435             440             445

Ile Val Gln Phe Asp Thr Glu Gly Ile Arg Ser Phe Phe Arg Thr Phe
450             455             460

Phe Arg Leu Pro Lys Trp Met Trp Gln Gly Phe Leu Gly Ser Thr Leu
465             470             475             480

Thr Ser Gly Asp Leu Val Leu Phe Ala Leu Tyr Met Phe Val Ile Ser
            485             490             495

Pro Asn Asn Leu Arg Lys Gly Leu Ile Asn His Leu Ile Ser Asp Pro
            500             505             510

Thr Gly Ala Thr Met Ile Lys Thr Tyr Leu Lys Val
            515             520

(2) INFORMATION FOR SEQ ID NO:3:

(i) SEQUENCE CHARACTERISTICS:
        (A) LENGTH: 956 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GCTCTTTCTC CTCCTCCTCT ACCGATTTCC GACTCCGCCT CCCGAAATCC TTATCCGGAT      60

TCTCTCCGTC TCTTCGATTT AAACGCTTTT CTGTCTGTTA CGTCGTCGAA GAACGGAGAC     120

AGAATTCTCC GATTGAGAAC GATGAGAGAC CGGAGAGCAC GAGCTCCACA AACGCTATAG     180

ACGCTGAGTA TCTGGCGTTG CGTTTGGCGG AGAAATTGGA GAGGAAGAAA TCGGAGAGGT     240

CCACTTATCT AATCGCTGCT ATGTTGTCGA GCTTTGGTAT CACTTCTATG CTGTTATGG      300

CTGTTTACTA CAGATTCTCT TGGCAAATGG AGGGAGGTGA GATCTCAATG TTGGAAATGT     360

TTGGTACATT TGCTCTCTCT GTTGGTGCTG CTGTTGGTAT GGAATTCTGG GCAAGATGGG     420

CTCATAGAGC TCTGTGGCAC GCTTCTCTAT GGAATATGCA TGAGTCACAT CACAAACCAA     480

GAGAAGGACC GTTTGAGCTA ACGATGTTT TTGCTATAGT GAACGCTGGT CCAGCGATTG      540

GTCTCCTCTC TTATGGATTC TTCAATAAAG GACTCGTTCC TGGTCTCTGC TTTGGCGCCG     600

GGTTAGGCAT AACGGTGTTT GGAATCGCCT ACATGTTTGT CCACGATGGT CTCGTGCACA     660
```

```
AGCGTTTCCC TGTAGGTCCC ATCGCCGACG TCCCTTACCT CCGAAAGGTC GCCGCCGCTC     720

ACCAGCTACA TCACACAGAC AAGTTCAATG GTGTACCATA TGGACTGTTT CTTGGACCCA     780

AGGAATTGGA AGAAGTTGGA GGAAATGAAG AGTTAGATAA GGAGATTAGT CGGAGAATCA     840

AATCATACAA AAAGGCCTCG GGCTCCGGGT CGAGTTCGAG TTCTTGACTT TAAACAAGTT     900

TTAAATCCCA AATTCTTTTT TTGTCTTCTG TCATTATGAT CATCTTAAGA CGGTCT         956
```

(2) INFORMATION FOR SEQ ID NO:4:

(i) SEQUENCE CHARACTERISTICS:
        (A) LENGTH: 294 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Ser Phe Ser Ser Ser Thr Asp Phe Arg Leu Arg Leu Pro Lys Ser
1               5                   10                  15

Leu Ser Gly Phe Ser Pro Ser Leu Arg Phe Lys Arg Phe Ser Val Cys
            20                  25                  30

Tyr Val Val Glu Glu Arg Arg Gln Asn Ser Pro Ile Glu Asn Asp Glu
        35                  40                  45

Arg Pro Glu Ser Thr Ser Ser Thr Asn Ala Ile Asp Ala Glu Tyr Leu
    50                  55                  60

Ala Leu Arg Leu Ala Glu Lys Leu Glu Arg Lys Lys Ser Glu Arg Ser
65                  70                  75                  80

Thr Tyr Leu Ile Ala Ala Met Leu Ser Ser Phe Gly Ile Thr Ser Met
                85                  90                  95

Ala Val Met Ala Val Tyr Tyr Arg Phe Ser Trp Gln Met Glu Gly Gly
            100                 105                 110

Glu Ile Ser Met Leu Glu Met Phe Gly Thr Phe Ala Leu Ser Val Gly
        115                 120                 125

Ala Ala Val Gly Met Glu Phe Trp Ala Arg Trp Ala His Arg Ala Leu
    130                 135                 140

Trp His Ala Ser Leu Trp Met Asn His Glu Ser His His Lys Pro Arg
145                 150                 155                 160

Glu Gly Pro Phe Glu Leu Asn Asp Val Phe Ala Ile Val Asn Ala Gly
                165                 170                 175

Pro Ala Ile Gly Leu Leu Ser Tyr Gly Phe Phe Asn Lys Gly Leu Val
            180                 185                 190

Pro Gly Leu Cys Phe Gly Ala Gly Leu Gly Ile Thr Val Phe Gly Ile
        195                 200                 205

Ala Tyr Met Phe Val His Asp Gly Leu Val His Lys Arg Phe Pro Val
    210                 215                 220

Gly Pro Ile Ala Asp Val Pro Tyr Leu Arg Lys Val Ala Ala His
225                 230                 235                 240

Gln Leu His His Thr Asp Lys Phe Asn Gly Val Pro Tyr Gly Leu Phe
                245                 250                 255

Leu Gly Pro Lys Glu Leu Glu Val Gly Gly Asn Glu Glu Leu Asp
            260                 265                 270

Lys Glu Ile Ser Arg Arg Ile Lys Ser Tyr Lys Lys Ala Ser Gly Ser
        275                 280                 285

Gly Ser Ser Ser Ser Ser
    290
```

(2) INFORMATION FOR SEQ ID NO:5:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Met Thr Gln Phe Leu Ile Val Val Ala Thr Val Leu Val Met Glu Leu
1               5                  10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
                35                  40                  45

Asn Asp Leu Tyr Gly Val Val Phe Ala Val Leu Ala Thr Ile Leu Phe
            50                  55                  60

Thr Val Gly Ala Tyr Trp Trp Pro Val Leu Trp Trp Ile Ala Leu Gly
65                  70                  75                  80

Met Thr Val Tyr Gly Leu Ile Tyr Phe Ile Leu His Asp Gly Leu Val
                85                  90                  95

His Gln Arg Trp Pro Phe Arg Tyr Ile Pro Arg Arg Gly Tyr Phe Arg
            100                 105                 110

Arg Leu Tyr Gln Ala His Arg Leu His His Ala Val Glu Gly Arg Asp
            115                 120                 125

His Cys Val Ser Phe Gly Phe Ile Tyr Ala Pro Pro Val Asp Lys Leu
            130                 135                 140

Lys Gln Asp Leu Lys Arg Ser Gly Val Leu Arg Pro Gln Asp Glu Arg
145                 150                 155                 160

Pro Ser
```

(2) INFORMATION FOR SEQ ID NO:6:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Leu Asn Ser Leu Ile Val Ile Leu Ser Val Ile Ala Met Glu Gly
1               5                  10                  15

Ile Ala Ala Phe Thr His Arg Tyr Ile Met His Gly Trp Gly Trp Arg
            20                  25                  30

Trp His Glu Ser His His Thr Pro Arg Lys Gly Val Phe Glu Leu Asn
            35                  40                  45

Asp Leu Phe Ala Val Val Phe Ala Gly Val Ala Ile Ala Leu Ile Ala
            50                  55                  60

Val Gly Thr Ala Gly Val Trp Pro Leu Gln Trp Ile Gly Cys Gly Met
65                  70                  75                  80

Thr Val Tyr Gly Leu Leu Tyr Phe Leu Val His Asp Gly Leu Val His
                85                  90                  95

Gln Arg Trp Pro Phe His Trp Ile Pro Arg Arg Gly Tyr Leu Lys Arg
            100                 105                 110
```

```
Leu Tyr Val Ala His Arg Leu His His Ala Val Arg Gly Arg Glu Gly
        115                 120                 125

Cys Val Ser Phe Gly Phe Ile Tyr Ala Arg Lys Pro Ala Asp Leu Gln
        130                 135                 140

Ala Ile Leu Arg Glu Arg His Gly Arg Pro Pro Lys Arg Asp Ala Ala
145                 150                 155                 160

Lys Asp Arg Pro Asp Ala Ala Ser Pro Ser Ser Ser Pro Glu
                165                 170                 175

(2) INFORMATION FOR SEQ ID NO:7:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Met Leu Trp Ile Trp Asn Ala Leu Ile Val Phe Val Thr Val Ile Gly
1               5                   10                  15

Met Glu Val Ile Ala Ala Leu Ala His Lys Tyr Ile Met His Gly Trp
            20                  25                  30

Gly Trp Gly Trp His Leu Ser His His Glu Pro Arg Lys Gly Ala Phe
        35                  40                  45

Glu Val Asn Asp Leu Tyr Ala Val Val Phe Ala Ala Leu Ser Ile Leu
    50                  55                  60

Leu Ile Tyr Leu Gly Ser Thr Gly Met Trp Pro Leu Gln Trp Ile Gly
65                  70                  75                  80

Ala Gly Met Thr Ala Tyr Gly Leu Leu Tyr Phe Met Val His Asp Gly
            85                  90                  95

Leu Val His Gln Arg Trp Pro Phe Arg Tyr Ile Pro Arg Lys Gly Tyr
        100                 105                 110

Leu Lys Arg Leu Tyr Met Ala His Arg Met His His Ala Val Arg Gly
        115                 120                 125

Lys Glu Gly Cys Val Ser Phe Gly Phe Leu Tyr Ala Pro Pro Leu Ser
        130                 135                 140

Lys Leu Gln Ala Thr Leu Arg Glu Arg His Gly Ala Arg Ala Gly Ala
145                 150                 155                 160

Ala Arg Asp Ala Gln Gly Gly Glu Asp Glu Pro Ala Ser Gly Lys
                165                 170                 175

(2) INFORMATION FOR SEQ ID NO:8:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Met Thr Asn Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
```

```
                35                  40                  45
Asn Asp Leu Tyr Gly Leu Val Phe Ala Val Ile Ala Thr Val Leu Phe
         50                  55                  60

Thr Val Gly Trp Ile Trp Ala Pro Val Leu Trp Trp Ile Ala Leu Gly
 65                  70                  75                  80

Met Thr Val Tyr Gly Leu Ile Tyr Phe Val Leu His Asp Gly Leu Val
                 85                  90                  95

His Trp Arg Trp Pro Phe Arg Tyr Ile Pro Arg Lys Gly Tyr Ala Arg
                100                 105                 110

Arg Leu Tyr Gln Ala His Arg Leu His His Ala Val Glu Gly Arg Asp
            115                 120                 125

His Cys Val Ser Phe Gly Phe Ile Tyr Ala Pro Pro Val Asp Lys Leu
        130                 135                 140

Lys Gln Asp Leu Lys Met Ser Gly Val Leu Arg Ala Glu Ala Gln Glu
145                 150                 155                 160

Arg Thr (2) INFORMATION FOR SEQ ID NO:9:

(i) SEQUENCE CHARACTERISTICS:
        (A) LENGTH: 954 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CCACGGGTCC GCCTCCCCGT TTTTTTCCGA TCCGATCTCC GGTGCCGAGG ACTCAGCTGT      60
TTGTTCGCGC TTTCTCAGCC GTCACCATGA CCGATTCTAA CGATGCTGGA ATGGATGCTG     120
TTCAGAGACG ACTCATGTTT GAAGACGAAT GCATTCTCGT TGATGAAAAT AATCGTGTGG     180
TGGGACATGA CACTAAGTAT AACTGTCATC TGATGGAAAA GATTGAAGCT GAGAATTTAC     240
TTCACAGAGC TTTCAGTGTG TTTTTATTCA ACTCCAAGTA TGAGTTGCTT CTCCAGCAAC     300
GGTCAAAAAC AAAGGTTACT TTCCCACTTG TGTGGACAAA CACTTGTTGC AGCCATCCTC     360
TTTACCGTGA ATCCGAGCTT ATTGAAGAGA ATGTGCTTGG TGTAAGAAAT GCCGCACAAA     420
GGAAGCTTTT CGATGAGCTC GGTATTGTAG CAGAAGATGT ACCAGTCGAT GAGTTCACTC     480
CCTTGGGACG CATGCTTTAC AAGGCACCTT CTGATGGGAA ATGGGGAGAG CACGAAGTTG     540
ACTATCTACT CTTCATCGTG CGGGATGTGA AGCTTCAACC AAACCCAGAT GAAGTGGCTG     600
AGATCAAGTA CGTGAGCAGG GAAGAGCTTA AGGAGCTGGT GAAGAAAGCA GATGCTGGCG     660
ATGAAGCTGT GAAACTATCT CCATGGTTCA GATTGGTGGT GGATAATTTC TTGATGAAGT     720
GGTGGGATCA TGTTGAGAAA GGAACTATCA CTGAAGCTGC AGACATGAAA ACCATTCACA     780
AGCTCTGAAC TTTCCATAAG TTTTGGATCT TCCCCTTCCC ATAATAAAAT TAAGAGATGA     840
GACTTTTATT GATTACAGAC AAAACTGGCA ACAAAATCTA TTCCTAGGAT TTTTTTTTGC     900
TTTTTATTTA CTTTTGATTC ATCTCTAGTT TAGTTTTCAT CTTAAAAAAA AAAA            954

(2) INFORMATION FOR SEQ ID NO:10:

(i) SEQUENCE CHARACTERISTICS:
        (A) LENGTH: 996 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO:10:

| | | | | | |
|---|---|---|---|---|---|
| CACCAATGTC | TGTTTCTTCT | TTATTTAATC | TCCCATTGAT | TCGCCTCAGA | TCTCTCGCTC | 60 |
| TTTCGTCTTC | TTTTTCTTCT | TTCCGATTTG | CCCATCGTCC | TCTGTCATCG | ATTTCACCGA | 120 |
| GAAAGTTACC | GAATTTTCGT | GCTTTCTCTG | GTACCGCTAT | GACAGATACT | AAAGATGCTG | 180 |
| GTATGGATGC | TGTTCAGAGA | CGTCTCATGT | TTGAGGATGA | ATGCATTCTT | GTTGATGAAA | 240 |
| CTGATCGTGT | TGTGGGGCAT | GTCAGCAAGT | ATAATTGTCA | TCTGATGGAA | ATATTGAAG | 300 |
| CCAAGAATTT | GCTGCACAGG | GCTTTTAGTG | TATTTTTATT | CAACTCGAAG | TATGAGTTGC | 360 |
| TTCTCCAGCA | AAGGTCAAAC | ACAAAGGTTA | CGTTCCCTCT | AGTGTGGACT | AACACTTGTT | 420 |
| GCAGCCATCC | TCTTTACCGT | GAATCAGAGC | TTATCCAGGA | CAATGCACTA | GGTGTGAGGA | 480 |
| ATGCTGCACA | AAGAAAGCTT | CTCGATGAGC | TTGGTATTGT | AGCTGAAGAT | GTACCAGTCG | 540 |
| ATGAGTTCAC | TCCCTTGGGA | CGTATGCTGT | ACAAGGCTCC | TTCTGATGGC | AAATGGGGAG | 600 |
| AGCATGAACT | TGATTACTTG | CTCTTCATCG | TGCGAGACGT | GAAGGTTCAA | CCAAACCCAG | 660 |
| ATGAAGTAGC | TGAGATCAAG | TATGTGAGCC | GGGAAGAGCT | GAAGGAGCTG | GTGAAGAAAG | 720 |
| CAGATGCAGG | TGAGGAAGGT | TTGAAACTGT | CACCATGGTT | CAGATTGGTG | GTGGACAATT | 780 |
| TCTTGATGAA | GTGGTGGGAT | CATGTTGAGA | AAGGAACTTT | GGTTGAAGCT | ATAGACATGA | 840 |
| AAACCATCCA | CAAACTCTGA | ACATCTTTTT | TTAAAGTTTT | TAAATCAATC | AACTTTCTCT | 900 |
| TCATCATTTT | TATCTTTTCG | ATGATAATAA | TTTGGGATAT | GTGAGACACT | TACAAAACTT | 960 |
| CCAAGCACCT | CAGGCAATAA | TAAAGTTTGC | GGCCGC | | | 996 |

(2) INFORMATION FOR SEQ ID NO:11:

(i) SEQUENCE CHARACTERISTICS:
        (A) LENGTH: 1165 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

| | | | | | |
|---|---|---|---|---|---|
| CTCGGTAGCT | GGCCACAATC | GCTATTTGGA | ACCTGGCCCG | GCGGCAGTCC | GATGCCGCGA | 60 |
| TGCTTCGTTC | GTTGCTCAGA | GGCCTCACGC | ATATCCCCCG | CGTGAACTCC | GCCCAGCAGC | 120 |
| CCAGCTGTGC | ACACGCGCGA | CTCCAGTTTA | AGCTCAGGAG | CATGCAGATG | ACGCTCATGC | 180 |
| AGCCCAGCAT | CTCAGCCAAT | CTGTCGCGCG | CCGAGGACCG | CACAGACCAC | ATGAGGGGTG | 240 |
| CAAGCACCTG | GGCAGGCGGG | CAGTCGCAGG | ATGAGCTGAT | GCTGAAGGAC | GAGTGCATCT | 300 |
| TGGTGGATGT | TGAGGACAAC | ATCACAGGCC | ATGCCAGCAA | GCTGGAGTGT | CACAAGTTCC | 360 |
| TACCACATCA | GCCTGCAGGC | CTGCTGCACC | GGGCCTTCTC | TGTGTTCCTG | TTTGACGATC | 420 |
| AGGGGCGACT | GCTGCTGCAA | CAGCGTGCAC | GCTCAAAAAT | CACCTTCCCA | AGTGTGTGGA | 480 |
| CGAACACCTG | CTGCAGCCAC | CCTTTACATG | GGCAGACCCC | AGATGAGGTG | GACCAACTAA | 540 |
| GCCAGGTGGC | CGACGGAACA | GTACCTGGCG | CAAAGGCTGC | TGCCATCCGC | AAGTTGGAGC | 600 |
| ACGAGCTGGG | GATACCAGCG | CACCAGCTGC | CGGCAAGCGC | GTTTCGCTTC | CTCACGCGTT | 660 |
| TGCACTACTG | TGCCGCGGAC | GTGCAGCCAG | CTGCGACACA | ATCAGCGCTC | TGGGGCGAGC | 720 |
| ACGAAATGGA | CTACATCTTG | TTCATCCGGG | CCAACGTCAC | CTTGGCGCCC | AACCCTGACG | 780 |
| AGGTGGACGA | AGTCAGGTAC | GTGACGCAAG | AGGAGCTGCG | GCAGATGATG | CAGCCGGACA | 840 |

```
ACGGGCTGCA ATGGTCGCCG TGGTTTCGCA TCATCGCCGC GCGCTTCCTT GAGCGTTGGT      900

GGGCTGACCT GGACGCGGCC CTAAACACTG ACAAACACGA GGATTGGGGA ACGGTGCATC      960

ACATCAACGA AGCGTGAAAG CAGAAGCTGC AGGATGTGAA GACACGTCAT GGGGTGGAAT     1020

TGCGTACTTG GCAGCTTCGT ATCTCCTTTT TCTGAGACTG AACCTGCAGT CAGGTCCCAC     1080

AAGGTCAGGT AAAATGGCTC GATAAAATGT ACCGTCACTT TTTGTCGCGT ATACTGAACT     1140

CCAAGAGGTC AAAAAAAAAA AAAAA                                          1165

(2) INFORMATION FOR SEQ ID NO:12:

(i) SEQUENCE CHARACTERISTICS:
        (A) LENGTH: 1135 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CTCGGTAGCT GGCCACAATC GCTATTTGGA ACCTGGCCCG GCGGCAGTCC GATGCCGCGA       60

TGCTTCGTTC GTTGCTCAGA GGCCTCACGC ATATCCGCG CGTGAACTCC GCCCAGCAGC      120

CCAGCTGTGC ACACGCGCGA CTCCAGTTTA AGCTCAGGAG CATGCAGCTG CTTTCCGAGG      180

ACCGCACAGA CCACATGAGG GGTGCAAGCA CCTGGGCAGG CGGGCAGTCG CAGGATGAGC      240

TGATGCTGAA GGACGAGTGC ATCTTGGTAG ATGTTGAGGA CAACATCACA GGCCATGCCA      300

GCAAGCTGGA GTGTCACAAG TTCCTACCAC ATCAGCCTGC AGGCCTGCTG CACCGGGCCT      360

TCTCTGTGTT CCTGTTTGAC GATCAGGGGC GACTGCTGCT GCAACAGCGT GCACGCTCAA      420

AAATCACCTT CCCAAGTGTG TGGACGAACA CCTGCTGCAG CCACCCTTTA CATGGGCAGA      480

CCCCAGATGA GGTGGACCAA CTAAGCCAGG TGGCCGACGG AACAGTACCT GGCGCAAAGG      540

CTGCTGCCAT CCGCAAGTTG GAGCACGAGC TGGGGATACC AGCGCACCAG CTGCCGGCAA      600

GCGCGTTTCG CTTCCTCACG CGTTTGCACT ACTGTGCCGC GGACGTGCAG CCAGCTGCGA      660

CACAATCAGC GCTCTGGGGC GAGCACGAAA TGGACTACAT CTTGTTCATC CGGGCCAACG      720

TCACCTTGGC GCCCAACCCT GACGAGGTGG ACGAAGTCAG GTACGTGACG CAAGAGGAGC      780

TGCGGCAGAT GATGCAGCCG GACAACGGGC TTCAATGGTC GCCGTGGTTT CGCATCATCG      840

CCGCGCGCTT CCTTGAGCGT TGGTGGGCTG ACCTGGACGC GGCCCTAAAC ACTGACAAAC      900

ACGAGGATTG GGAACGGTG CATCACATCA ACGAAGCGTG AAGGCAGAAG CTGCAGGATG      960

TGAAGACACG TCATGGGGTG GAATTGCGTA CTTGGCAGCT TCGTATCTCC TTTTTCTGAG     1020

ACTGAACCTG CAGAGCTAGA GTCAATGGTG CATCATATTC ATCGTCTCTC TTTTGTTTTA     1080

GACTAATCTG TAGCTAGAGT CACTGATGAA TCCTTTACAA CTTTCAAAAA AAAAA          1135

(2) INFORMATION FOR SEQ ID NO:13:

(i) SEQUENCE CHARACTERISTICS:
        (A) LENGTH: 960 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCAAAAACAA CTCAAATCTC CTCCGTCGCT CTTACTCCGC CATGGGTGAC GACTCCGGCA       60

TGGATGCTGT TCAGCGACGT CTCATGTTTG ACGATGAATG CATTTTGGTG GATGAGTGTG      120
```

```
ACAATGTGGT GGGACATGAT ACCAAATACA ATTGTCACTT GATGGAGAAG ATTGAAACAG      180

GTAAAATGCT GCACAGAGCA TTCAGCGTTT TTCTATTCAA TTCAAAATAC GAGTTACTTC      240

TTCAGCAACG GTCTGCAACC AAGGTGACAT TTCCTTTAGT ATGGACCAAC ACCTGTTGCA      300

GCCATCCACT CTACAGAGAA TCCGAGCTTG TTCCCGAAAC GCCTGAGAGA ATGCTGCACA      360

GAGGANNNNN NNNNNNNNNN NNNNNNNNNN NNNNNNNNNN NNNNNNNNNN NNNNNNNNNN      420

NNNNNNNNNN NNNNNNNNNN NNNNNNNNNN NNNNNNNNNN NNNNNNNNNN NNNNNNNNNN      480

NNNNNNNNNN NNNNNNNNNN NNNNNNNNNN NNNNNNNNNN NNNNNNNNNN NNNNNNNNNN      540

NNNNNNNNNN NNNNNNNNNN NNNNNNNNNN NNNNNNNNNN NNNNNNNNNN NNNNNNNNNN      600

NNNNNNNNNN NNNNNNNNNN NNNNNNNNNN NNNNNNNNNN NNNNNNNNNN NNNNNNNNNN      660

NNNNNNNNNN NNNNNNNNNN TCATGTGCAA AAGGGTACAC TCACTGAATG CAATTTGATA      720

TGAAAACCAT ACACAAGCTG ATATAGAAAC ACACCCTCAA CCGAAAAGCA AGCCTAATAA      780

TTCGGGTTGG GTCGGGTCTA CCATCAATTG TTTTTTTCTT TTAACAACTT TTAATCTCTA      840

TTTGAGCATG TTGATTCTTG TCTTTTGTGT GTAAGATTTT GGGTTTCGTT TCAGTTGTAA      900

TAATGAACCA TTGATGGTTT GCAATTTCAA GTTCCTATCG ACATGTAGTG ATCTAAAAAA      960
```

(2) INFORMATION FOR SEQ ID NO:14:

(i) SEQUENCE CHARACTERISTICS:
  (A) LENGTH: 305 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:14:

```
Met Leu Arg Ser Leu Leu Arg Gly Leu Thr His Ile Pro Arg Val Asn
  1               5                  10                  15

Ser Ala Gln Gln Pro Ser Cys Ala His Ala Arg Leu Gln Phe Lys Leu
             20                  25                  30

Arg Ser Met Gln Met Thr Leu Met Gln Pro Ser Ile Ser Ala Asn Leu
         35                  40                  45

Ser Arg Ala Glu Asp Arg Thr Asp His Met Arg Gly Ala Ser Thr Trp
 50                  55                  60

Ala Gly Gln Ser Gln Asp Glu Leu Met Leu Lys Asp Glu Cys Ile
 65                  70                  75                  80

Leu Val Asp Val Glu Asp Asn Ile Thr Gly His Ala Ser Lys Leu Glu
                 85                  90                  95

Cys His Lys Phe Leu Pro His Gln Pro Ala Gly Leu Leu His Arg Ala
            100                 105                 110

Phe Ser Val Phe Leu Phe Asp Asp Gln Gly Arg Leu Leu Leu Gln Gln
        115                 120                 125

Arg Ala Arg Ser Lys Ile Thr Phe Pro Ser Val Trp Thr Asn Thr Cys
    130                 135                 140

Cys Ser His Pro Leu His Gly Gln Thr Pro Asp Glu Val Asp Gln Leu
145                 150                 155                 160

Ser Gln Val Ala Asp Gly Thr Val Pro Gly Ala Lys Ala Ala Ile
                165                 170                 175

Arg Lys Leu Glu His Glu Leu Gly Ile Pro Ala His Gln Leu Pro Ala
            180                 185                 190

Ser Ala Phe Arg Phe Leu Thr Arg Leu His Tyr Cys Ala Ala Asp Val
```

```
                195                 200                 205
Gln Pro Ala Thr Gln Ser Ala Leu Trp Gly Glu His Glu Met Asp
    210                 215                 220

Tyr Ile Leu Phe Ile Arg Ala Asn Val Thr Leu Ala Pro Asn Pro Asp
225                 230                 235                 240

Glu Val Asp Glu Val Arg Tyr Val Thr Gln Glu Glu Leu Arg Gln Met
                245                 250                 255

Met Gln Pro Asp Asn Gly Leu Gln Trp Ser Pro Trp Phe Arg Ile Ile
        260                 265                 270

Ala Ala Arg Phe Leu Glu Arg Trp Trp Ala Asp Leu Asp Ala Ala Leu
            275                 280                 285

Asn Thr Asp Lys His Glu Asp Trp Gly Thr Val His His Ile Asn Glu
    290                 295                 300

Ala
305

(2) INFORMATION FOR SEQ ID NO:15:

(i) SEQUENCE CHARACTERISTICS:
        (A) LENGTH: 293 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Met Leu Arg Ser Leu Leu Arg Gly Leu Thr His Ile Pro Arg Val Asn
1               5                   10                  15

Ser Ala Gln Gln Pro Ser Cys Ala His Ala Arg Leu Gln Phe Lys Leu
                20                  25                  30

Arg Ser Met Gln Leu Leu Ser Glu Asp Arg Thr Asp His Met Arg Gly
            35                  40                  45

Ala Ser Thr Trp Ala Gly Gly Gln Ser Gln Asp Glu Leu Met Leu Lys
        50                  55                  60

Asp Glu Cys Ile Leu Val Asp Val Glu Asp Asn Ile Thr Gly His Ala
65                  70                  75                  80

Ser Lys Leu Glu Cys His Lys Phe Leu Pro His Gln Pro Ala Gly Leu
                85                  90                  95

Leu His Arg Ala Phe Ser Val Phe Leu Phe Asp Asp Gln Gly Arg Leu
                100                 105                 110

Leu Leu Gln Gln Arg Ala Arg Ser Lys Ile Thr Phe Pro Ser Val Trp
            115                 120                 125

Thr Asn Thr Cys Cys Ser His Pro Leu His Gly Gln Thr Pro Asp Glu
    130                 135                 140

Val Asp Gln Leu Ser Gln Val Ala Asp Gly Thr Val Pro Gly Ala Lys
145                 150                 155                 160

Ala Ala Ala Ile Arg Lys Leu Glu His Glu Leu Gly Ile Pro Ala His
                165                 170                 175

Gln Leu Pro Ala Ser Ala Phe Arg Phe Leu Thr Arg Leu His Tyr Cys
                180                 185                 190

Ala Ala Asp Val Gln Pro Ala Ala Thr Gln Ser Ala Leu Trp Gly Glu
            195                 200                 205

His Glu Met Asp Tyr Ile Leu Phe Ile Arg Ala Asn Val Thr Leu Ala
    210                 215                 220

Pro Asn Pro Asp Glu Val Asp Glu Val Arg Tyr Val Thr Gln Glu Glu
```

```
                    225                 230                 235                 240
Leu Arg Gln Met Met Gln Pro Asp Asn Gly Leu Gln Trp Ser Pro Trp
                    245                 250                 255
Phe Arg Ile Ile Ala Ala Arg Phe Leu Glu Arg Trp Trp Ala Asp Leu
                260                 265                 270
Asp Ala Ala Leu Asn Thr Asp Lys His Glu Asp Trp Gly Thr Val His
            275                 280                 285
His Ile Asn Glu Ala
        290
```

(2) INFORMATION FOR SEQ ID NO:16:

(i) SEQUENCE CHARACTERISTICS:
        (A) LENGTH: 284 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Met Ser Val Ser Ser Leu Phe Asn Leu Pro Leu Ile Arg Leu Arg Ser
1               5                   10                  15
Leu Ala Leu Ser Ser Ser Phe Ser Phe Arg Phe Ala His Arg Pro
                20                  25                  30
Leu Ser Ser Ile Ser Pro Arg Lys Leu Pro Asn Phe Arg Ala Phe Ser
            35                  40                  45
Gly Thr Ala Met Thr Asp Thr Lys Asp Ala Gly Met Asp Ala Val Gln
        50                  55                  60
Arg Arg Leu Met Phe Glu Asp Glu Cys Ile Leu Val Asp Glu Thr Asp
65                  70                  75                  80
Arg Val Val Gly His Val Ser Lys Tyr Asn Cys His Leu Met Glu Asn
                85                  90                  95
Ile Glu Ala Lys Asn Leu Leu His Arg Ala Phe Ser Val Phe Leu Phe
            100                 105                 110
Asn Ser Lys Tyr Glu Leu Leu Leu Gln Gln Arg Ser Asn Thr Lys Val
        115                 120                 125
Thr Phe Pro Leu Val Trp Thr Asn Thr Cys Cys Ser His Pro Leu Tyr
    130                 135                 140
Arg Glu Ser Glu Leu Ile Gln Asp Asn Ala Leu Gly Val Arg Asn Ala
145                 150                 155                 160
Ala Gln Arg Lys Leu Leu Asp Glu Leu Gly Ile Val Ala Glu Asp Val
                165                 170                 175
Pro Val Asp Glu Phe Thr Pro Leu Gly Arg Met Leu Tyr Lys Ala Pro
            180                 185                 190
Ser Asp Gly Lys Trp Gly Glu His Glu Leu Asp Tyr Leu Leu Phe Ile
        195                 200                 205
Val Arg Asp Val Lys Val Gln Pro Asn Pro Asp Glu Val Ala Glu Ile
    210                 215                 220
Lys Tyr Val Ser Arg Glu Glu Leu Lys Glu Leu Val Lys Lys Ala Asp
225                 230                 235                 240
Ala Gly Glu Glu Gly Leu Lys Leu Ser Pro Trp Phe Arg Leu Val Val
                245                 250                 255
Asp Asn Phe Leu Met Lys Trp Trp Asp His Val Glu Lys Gly Thr Leu
            260                 265                 270
Val Glu Ala Ile Asp Met Lys Thr Ile His Lys Leu
```

275          280

(2) INFORMATION FOR SEQ ID NO:17:

(i) SEQUENCE CHARACTERISTICS:
       (A) LENGTH: 287 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:17:

Met Ser Ser Ser Met Leu Asn Phe Thr Ala Ser Arg Ile Val Ser Leu
1               5                   10                  15

Pro Leu Leu Ser Ser Pro Ser Arg Val His Leu Pro Leu Cys Phe
            20                  25                  30

Phe Ser Pro Ile Ser Leu Thr Gln Arg Phe Ser Ala Lys Leu Thr Phe
            35                  40                  45

Ser Ser Gln Ala Thr Thr Met Gly Glu Val Val Asp Ala Gly Met Asp
            50                  55                  60

Ala Val Gln Arg Arg Leu Met Phe Glu Asp Glu Cys Ile Leu Val Asp
65                  70                  75                  80

Glu Asn Asp Lys Val Val Gly His Glu Ser Lys Tyr Asn Cys His Leu
                85                  90                  95

Met Glu Lys Ile Glu Ser Glu Asn Leu Leu His Arg Ala Phe Ser Val
                100                 105                 110

Phe Leu Phe Asn Ser Lys Tyr Glu Leu Leu Leu Gln Gln Arg Ser Ala
            115                 120                 125

Thr Lys Val Thr Phe Pro Leu Val Trp Thr Asn Thr Cys Cys Ser His
130                 135                 140

Pro Leu Tyr Arg Glu Ser Glu Leu Ile Asp Glu Asn Cys Leu Gly Val
145                 150                 155                 160

Arg Asn Ala Ala Gln Arg Lys Leu Leu Asp Glu Leu Gly Ile Pro Ala
                165                 170                 175

Glu Asp Leu Pro Val Asp Gln Phe Ile Pro Leu Ser Arg Ile Leu Tyr
                180                 185                 190

Lys Ala Pro Ser Asp Gly Lys Trp Gly Glu His Glu Leu Asp Tyr Leu
            195                 200                 205

Leu Phe Ile Ile Arg Asp Val Asn Leu Asp Pro Asn Pro Asp Glu Val
210                 215                 220

Ala Glu Val Lys Tyr Met Asn Arg Asp Asp Leu Lys Glu Leu Leu Arg
225                 230                 235                 240

Lys Ala Asp Ala Glu Glu Glu Gly Val Lys Leu Ser Pro Trp Phe Arg
                245                 250                 255

Leu Val Val Asp Asn Phe Leu Phe Lys Trp Trp Asp His Val Glu Lys
                260                 265                 270

Gly Ser Leu Lys Asp Ala Ala Asp Met Lys Thr Ile His Lys Leu
            275                 280                 285

(2) INFORMATION FOR SEQ ID NO:18:

(i) SEQUENCE CHARACTERISTICS:
       (A) LENGTH: 261 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:18:

```
Thr Gly Pro Pro Pro Arg Phe Phe Pro Ile Arg Ser Pro Val Pro Arg
1               5                  10                  15

Thr Gln Leu Phe Val Arg Ala Phe Ser Ala Val Thr Met Thr Asp Ser
            20                  25                  30

Asn Asp Ala Gly Met Asp Ala Val Gln Arg Arg Leu Met Phe Glu Asp
        35                  40                  45

Glu Cys Ile Leu Val Asp Glu Asn Asn Arg Val Val Gly His Asp Thr
    50                  55                  60

Lys Tyr Asn Cys His Leu Met Glu Lys Ile Glu Ala Glu Asn Leu Leu
65                  70                  75                  80

His Arg Ala Phe Ser Val Phe Leu Phe Asn Ser Lys Tyr Glu Leu Leu
                85                  90                  95

Leu Gln Gln Arg Ser Lys Thr Lys Val Thr Phe Pro Leu Val Trp Thr
            100                 105                 110

Asn Thr Cys Cys Ser His Pro Leu Tyr Arg Glu Ser Glu Leu Ile Glu
        115                 120                 125

Glu Asn Val Leu Gly Val Arg Asn Ala Ala Gln Arg Lys Leu Phe Asp
    130                 135                 140

Glu Leu Gly Ile Val Ala Glu Asp Val Pro Val Asp Glu Phe Thr Pro
145                 150                 155                 160

Leu Gly Arg Met Leu Tyr Lys Ala Pro Ser Asp Gly Lys Trp Gly Glu
                165                 170                 175

His Glu Val Asp Tyr Leu Leu Phe Ile Val Arg Asp Val Lys Leu Gln
            180                 185                 190

Pro Asn Pro Asp Glu Val Ala Glu Ile Lys Tyr Val Ser Arg Glu Glu
        195                 200                 205

Leu Lys Glu Leu Val Lys Lys Ala Asp Ala Gly Asp Glu Ala Val Lys
    210                 215                 220

Leu Ser Pro Trp Phe Arg Leu Val Val Asp Asn Phe Leu Met Lys Trp
225                 230                 235                 240

Trp Asp His Val Glu Lys Gly Thr Ile Thr Glu Ala Ala Asp Met Lys
                245                 250                 255

Thr Ile His Lys Leu
            260
```

(2) INFORMATION FOR SEQ ID NO:19:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Met Thr Ala Asp Asn Asn Ser Met Pro His Gly Ala Val Ser Ser Tyr
1               5                  10                  15

Ala Lys Leu Val Gln Asn Gln Thr Pro Glu Asp Ile Leu Glu Glu Phe
            20                  25                  30

Pro Glu Ile Ile Pro Leu Gln Gln Arg Pro Asn Thr Arg Ser Ser Glu
        35                  40                  45

Thr Ser Asn Asp Glu Ser Gly Glu Thr Cys Phe Ser Gly His Asp Glu
    50                  55                  60
```

-continued

```
Glu Gln Ile Lys Leu Met Asn Glu Asn Cys Ile Val Leu Asp Trp Asp
 65                  70                  75                  80

Asp Asn Ala Ile Gly Ala Gly Thr Lys Lys Val Cys His Leu Met Glu
                 85                  90                  95

Asn Ile Glu Lys Gly Leu Leu His Arg Ala Phe Ser Val Phe Ile Phe
                100                 105                 110

Asn Glu Gln Gly Glu Leu Leu Leu Gln Gln Arg Ala Thr Glu Lys Ile
                115                 120                 125

Thr Phe Pro Asp Leu Trp Thr Asn Thr Cys Cys Ser His Pro Leu Cys
130                 135                 140

Ile Asp Asp Glu Leu Gly Leu Lys Gly Lys Leu Asp Asp Lys Ile Lys
145                 150                 155                 160

Gly Ala Ile Thr Ala Ala Val Arg Lys Leu Asp His Glu Leu Gly Ile
                165                 170                 175

Pro Glu Asp Glu Thr Lys Thr Arg Gly Lys Phe His Phe Leu Asn Arg
                180                 185                 190

Ile His Tyr Met Ala Pro Ser Asn Glu Pro Trp Gly Glu His Glu Ile
                195                 200                 205

Asp Tyr Ile Leu Phe Tyr Lys Ile Asn Ala Lys Glu Asn Leu Thr Val
210                 215                 220

Asn Pro Asn Val Asn Glu Val Arg Asp Phe Lys Trp Val Ser Pro Asn
225                 230                 235                 240

Asp Leu Lys Thr Met Phe Ala Asp Pro Ser Tyr Lys Phe Thr Pro Trp
                245                 250                 255

Phe Lys Ile Ile Cys Glu Asn Tyr Leu Phe Asn Trp Trp Glu Gln Leu
                260                 265                 270

Asp Asp Leu Ser Glu Val Glu Asn Asp Arg Gln Ile His Arg Met Leu
                275                 280                 285

(2) INFORMATION FOR SEQ ID NO:20:

(i) SEQUENCE CHARACTERISTICS:
        (A) LENGTH: 456 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Met Asp Thr Leu Leu Lys Thr Pro Asn Leu Glu Phe Leu Pro His Gly
 1                   5                  10                  15

Phe Val Lys Ser Phe Ser Lys Phe Gly Lys Cys Glu Gly Val Cys Val
                 20                  25                  30

Lys Ser Ser Ala Leu Leu Glu Leu Val Pro Glu Thr Lys Lys Glu Asn
                 35                  40                  45

Leu Asp Phe Glu Leu Pro Met Tyr Asp Pro Ser Lys Gly Val Val Asp
 50                  55                  60

Leu Ala Val Val Gly Gly Gly Pro Ala Gly Leu Ala Val Ala Gln Gln
 65                  70                  75                  80

Val Ser Glu Ala Gly Leu Ser Val Cys Ser Ile Asp Pro Pro Lys Leu
                 85                  90                  95

Ile Trp Pro Asn Asn Tyr Gly Val Trp Val Asp Glu Phe Glu Ala Met
                100                 105                 110

Asp Leu Leu Asp Cys Leu Asp Ala Thr Trp Ser Gly Ala Val Tyr Ile
                115                 120                 125
```

```
Asp Asp Thr Lys Asp Leu Arg Pro Tyr Gly Arg Val Asn Arg Lys Gln
    130                 135                 140

Leu Lys Ser Lys Met Met Gln Lys Cys Ile Asn Gly Val Lys Phe His
145                 150                 155                 160

Gln Ala Lys Val Ile Lys Val Ile His Glu Glu Lys Ser Met Leu Ile
                165                 170                 175

Cys Asn Asp Gly Thr Ile Gln Ala Thr Val Val Leu Asp Ala Thr Gly
                180                 185                 190

Phe Ser Arg Leu Val Gln Tyr Asp Lys Pro Tyr Asn Pro Gly Tyr Gln
                195                 200                 205

Val Ala Tyr Gly Ile Leu Ala Glu Val Glu Glu His Pro Phe Asp Lys
    210                 215                 220

Met Val Phe Met Asp Trp Arg Asp Ser His Leu Asn Asn Glu Leu Lys
225                 230                 235                 240

Glu Arg Asn Ser Ile Pro Thr Phe Leu Tyr Ala Met Pro Phe Ser Ser
                245                 250                 255

Asn Arg Ile Phe Leu Glu Glu Thr Ser Leu Val Ala Arg Pro Gly Leu
                260                 265                 270

Arg Met Asp Asp Ile Gln Glu Arg Met Val Ala Arg Leu His Leu Gly
    275                 280                 285

Ile Lys Val Lys Ser Ile Glu Glu Asp Glu His Cys Val Ile Pro Met
290                 295                 300

Gly Gly Pro Leu Pro Val Leu Pro Gln Arg Val Val Gly Ile Gly Gly
305                 310                 315                 320

Thr Ala Gly Met Val His Pro Ser Thr Gly Tyr Met Val Ala Arg Thr
                325                 330                 335

Leu Ala Ala Ala Pro Val Val Ala Asn Ala Ile Ile Tyr Leu Gly Ser
                340                 345                 350

Glu Ser Ser Gly Glu Leu Ser Ala Glu Val Trp Lys Asp Leu Trp Pro
    355                 360                 365

Ile Glu Arg Arg Arg Gln Arg Glu Phe Phe Cys Phe Gly Met Asp Ile
    370                 375                 380

Leu Leu Lys Leu Asp Leu Pro Ala Thr Arg Arg Phe Asp Ala Phe
385                 390                 395                 400

Phe Asp Leu Glu Pro Arg Tyr Trp His Gly Phe Leu Ser Ser Arg Leu
                405                 410                 415

Phe Leu Pro Glu Leu Ile Val Phe Gly Leu Ser Leu Phe Ser His Ala
                420                 425                 430

Ser Asn Thr Ser Arg Glu Ile Met Thr Lys Gly Thr Pro Leu Val Met
                435                 440                 445

Ile Asn Asn Leu Leu Gln Asp Glu
    450                 455

(2) INFORMATION FOR SEQ ID NO:21:

(i) SEQUENCE CHARACTERISTICS:
        (A) LENGTH: 524 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Met Glu Cys Val Gly Ala Arg Asn Phe Ala Ala Met Ala Val Ser Thr
1               5                   10                  15
```

```
Phe Pro Ser Trp Ser Cys Arg Arg Lys Phe Pro Val Val Lys Arg Tyr
            20                  25                  30

Ser Tyr Arg Asn Ile Arg Phe Gly Leu Cys Ser Val Arg Ala Ser Gly
            35                  40                  45

Gly Gly Ser Ser Gly Ser Glu Ser Cys Val Ala Val Arg Glu Asp Phe
        50                  55                  60

Ala Asp Glu Glu Asp Phe Val Lys Ala Gly Ser Glu Ile Leu Phe
65                  70                  75                  80

Val Gln Met Gln Gln Asn Lys Asp Met Asp Glu Gln Ser Lys Leu Val
                85                  90                  95

Asp Lys Leu Pro Pro Ile Ser Ile Gly Asp Gly Ala Leu Asp His Val
            100                 105                 110

Val Ile Gly Cys Gly Pro Ala Gly Leu Ala Leu Ala Ala Glu Ser Ala
            115                 120                 125

Lys Leu Gly Leu Lys Val Gly Leu Ile Gly Pro Asp Leu Pro Phe Thr
        130                 135                 140

Asn Asn Tyr Gly Val Trp Glu Asp Glu Phe Asn Asp Leu Gly Leu Gln
145                 150                 155                 160

Lys Cys Ile Glu His Val Trp Arg Glu Thr Ile Val Tyr Leu Asp Asp
                165                 170                 175

Asp Lys Pro Ile Thr Ile Gly Arg Ala Tyr Gly Arg Val Ser Arg Arg
            180                 185                 190

Leu Leu His Glu Glu Leu Leu Arg Arg Cys Val Glu Ser Gly Val Ser
            195                 200                 205

Tyr Leu Ser Ser Lys Val Asp Ser Ile Thr Glu Ala Ser Asp Gly Leu
        210                 215                 220

Arg Leu Val Ala Cys Asp Asp Asn Asn Val Ile Pro Cys Arg Leu Ala
225                 230                 235                 240

Thr Val Ala Ser Gly Ala Ala Ser Gly Lys Leu Leu Gln Tyr Glu Val
                245                 250                 255

Gly Gly Pro Arg Val Cys Val Gln Thr Ala Tyr Gly Val Glu Val Glu
            260                 265                 270

Val Glu Asn Ser Pro Tyr Asp Pro Asp Gln Met Val Phe Met Asp Tyr
            275                 280                 285

Arg Asp Tyr Thr Asn Glu Lys Val Arg Ser Leu Glu Ala Glu Tyr Pro
        290                 295                 300

Thr Phe Leu Tyr Ala Met Pro Met Thr Lys Ser Arg Leu Phe Phe Glu
305                 310                 315                 320

Glu Thr Cys Leu Ala Ser Lys Asp Val Met Pro Phe Asp Leu Leu Lys
                325                 330                 335

Thr Lys Leu Met Leu Arg Leu Asp Thr Leu Gly Ile Arg Ile Leu Lys
            340                 345                 350

Thr Tyr Glu Glu Glu Trp Ser Tyr Ile Pro Val Gly Gly Ser Leu Pro
        355                 360                 365

Asn Thr Glu Gln Lys Asn Leu Ala Phe Gly Ala Ala Ala Ser Met Val
        370                 375                 380

His Pro Ala Thr Gly Tyr Ser Val Val Arg Ser Leu Ser Glu Ala Pro
385                 390                 395                 400

Lys Tyr Ala Ser Val Ile Ala Glu Ile Leu Arg Glu Glu Thr Thr Lys
                405                 410                 415

Gln Ile Asn Ser Asn Ile Ser Arg Gln Ala Trp Asp Thr Leu Trp Pro
            420                 425                 430

Pro Glu Arg Lys Arg Gln Arg Ala Phe Phe Leu Phe Gly Leu Ala Leu
```

-continued

```
                435                 440                 445
Ile Val Gln Phe Asp Thr Glu Gly Ile Arg Ser Phe Phe Arg Thr Phe
    450                 455                 460

Phe Arg Leu Pro Lys Trp Met Trp Gln Gly Phe Leu Gly Ser Thr Leu
465             470                 475                 480

Thr Ser Gly Asp Leu Val Leu Phe Ala Leu Tyr Met Phe Val Ile Ser
            485                 490                 495

Pro Asn Asn Leu Arg Lys Gly Leu Ile Asn His Leu Ile Ser Asp Pro
                500                 505                 510

Thr Gly Ala Thr Met Ile Lys Thr Tyr Leu Lys Val
            515                 520
```